US006004764A

United States Patent [19]

[11] Patent Number: 6,004,764
[45] Date of Patent: Dec. 21, 1999

Bishai et al.

[54] **METHOD OF IDENTIFYING COMPOUNDS THAT REGULATE THE BINDING OF *M. TUBERCULOSIS* SIGF TO *M. TUBERCULOSIS* ORFX**

[75] Inventors: William R. Bishai, Baltimore, Md.; Douglas B. Young, London, United Kingdom; Ying Zhang, Baltimore, Md.; James DeMaio, Tacoma, Wash.

[73] Assignee: Johns Hopkins University, Baltimore, Md.

[21] Appl. No.: 08/826,390

[22] Filed: Apr. 9, 1997

Related U.S. Application Data

[63] Continuation-in-part of application No. 08/622,352, Mar. 27, 1996, Pat. No. 5,824,546, and a continuation-in-part of application No. 08/622,353, Mar. 27, 1996, Pat. No. 5,700, 925.

[51] Int. Cl.[6] .................................................. G01N 33/566
[52] U.S. Cl. .............................................................. 435/7.8
[58] Field of Search ............................................... 435/7.8

[56] References Cited

PUBLICATIONS

Smith and Moss, In *Tuberculosis: Pathogenesis Protection, and Control,* Bloom, ed. (ASM Press, Washington, D.C.), pp. 47–59 (1994).
Bloom and Murray, Science, 257:1055–1064 (1992).
Gedde–Dahl, Am. J. Hyg. 56:139–214 (1952).
Sudre et al., Bull WHO, 70:149–159 (1992).
Wayne, Eur. J. Clin. Microbiol. Infectious Diseases, 13:908–914 (1994).
Khomenko et al., "L–transformation of the mycobacterial population in the process of treating patients with newly detected destructive pulmonary tuberculosis", Probl. Tuberk, 2:18–23 (1980).
Werner, Am. Rev. Tuberculosis, 69:473–474 (1953).
Ausubel et al., eds. *Current Protocols in Molecular Biology* (John Wiley, New York), pp. 1.8.4–1.8.8 (1994).
Sambrook et al., eds. *Molecular Cloning: A Laboratory Manual* (Cold Spring Harbor Lab. Press, Plainview, NY), pp. 9.31–9.57 (1989).
Wayne, Am. Rev. Respiratory Disease, 114:807–811 (1976).
Firestein et al., Anal. Biochem., 167:381–386 (1987).
Lonetto et al., J. Bacteriol., 174:3843–3849 (1992).
Gross et al., In *Transcriptional Regulation,* McKnight et al., eds. (Cold Spring Habor Lab. Press, Plainview, NY), 1:129–176 (1992).
Predich et al., Mol. Microbiol., 15:355–366 (1995).
Kempsell et al., Gen. Microbiol., 138:1717–1727 (1992).
Honore et al., Mol. Microbiol., 7:207–214 (1993).
Tanaka et al., Science, 242:1040–1042 (1988).
Potuckova et al., Mol. Microbiol., 17:37–48 (1995).
Gholamhoseinian et al., J. Bacteriol., 171:5747–5749 (1989).
Margolis et al., Science, 254:562–565 (1991).
Benson and Haldenwang, J. Bacteriol., 175:2347–2356 (1993).
Moran, In *Molecular Biological Methods for Bacillus,* Harwood and Cutting, eds. (Wiley & Sons, Chichester, England), pp. 267–293 (1990).
Lonetto et al., Proc. Natl. Acad. Sci. USA, 91:7573–7577 (1994).
Haines and Gillespie, Biotechniques, 12:736–740 (1992).
Spiegelman and Whiteley, J. Biol. Chem., 249:1476–1482 (1974).
Benson and Haldenwang, Proc. Natl. Acad. Sci. USA, 90:2330–2334 (1993).
Schmidt et al., Proc. Natl. Acad. Sci. USA, 87:9221–9225 (1990).
Alper et al., Cell, 77:195–205 (1994).
Schuler et al., Proteins: Struct. Funct. Genet., 9:180–190 (1991).
Stanford, Tubercle, 68:241–242 (1987).
Csillag, J. Gen. Microbiol., 34:341–352 (1964).
Khomenko, Tubercle, 68:243–253 (1987).
Barksdale et al., Biochem. Biophys. Res. Comm., 54:290–296 (1973).
Chatterjee, Leprosy in India, 48:398–405 (1976).
Rook and Stanford, Immunol. Today, 13:160–164 (1992).
Fidler et al., Brit. Med. J., 306:546–549 (1993).
Haldenwang, Microbiol. Rev., 59:1–30 (1995).
Dufour and Haldenwang, J. Bacteriol., 176:1813–1820 (1994).
Kalman et al., J. Bacteriol., 172:5575–5585 (1990).
Min et al., Cell, 74:735–742 (1993).
Stock et al., Microbiol. Rev., 53:450–490 (1989).
Boylan et al., J. Bacteriol., 175:3957–3963 (1993).
Burgess and Travers, Methods Enzymol., 21:500–506 (1971).
Kumar and Chatterji, J. Biochem. Biophys. Methods, 15:235–240 (1988).
Bashyam et al, J. Bateriol., 178:4847–4853 (1996).
Bishai et al, New Eng. J. Med., 334:1572–1576 (1996).
Collins et al., Proc. Natl. Acad. Sci. USA, 92:8036–8040 (1995).
Curcic et al, Mol. Microbiol., 13:1057–1064 (1994).
DeMaio et al., Proc. Natl. Acad. Sci. USA, 93:2790–2794 (1996).
Dhandayuthapani et al., Mol. Microbiol., 17:901–912 (1995).
Errington and Mandelstam, J. Gen. Microbiol., 132:2967–2976 (1986).
Gordon et al., Lett. Appl. Microbiol., 19:336–340 (1994).
Wu et al., J. Bacteriol., 171:692–698 (1989).
DeMaio et al., "Mycobacterium tuberculosis sigF is part of a gene cluster with similarities to the *Bacillus subtilis* sigF and sigB operons"; Tubercle and Lung Disease, (1997) 78(1), pp. 1–10, in press.
Ngo et al, The Protein Folding Problem and Tertiary Structure Prediction, Mertz et al (eds.), Birkhauser, Boston, pp. 433 and 492–495, 1994.

*Primary Examiner*—Terry McKelvey
*Attorney, Agent, or Firm*—Cushman Darby & Cushman; IP Group of Pillsbury; Madison & Sutro

[57] ABSTRACT sigF is a gene that controls *M. tuberculosis* latency. A diagnostic test for latent tuberculosis involves detecting *M. tuberculosis* sigF in clinical specimens. Two genes orfX and orfY regulate sigF expression and sigF activity. *M. tuberculosis* sigF, orfX, and orfY are used in screening methods for potential therapeutic agents which regulate the growth of *M. tuberculosis.*

8 Claims, 5 Drawing Sheets

FIG. IA
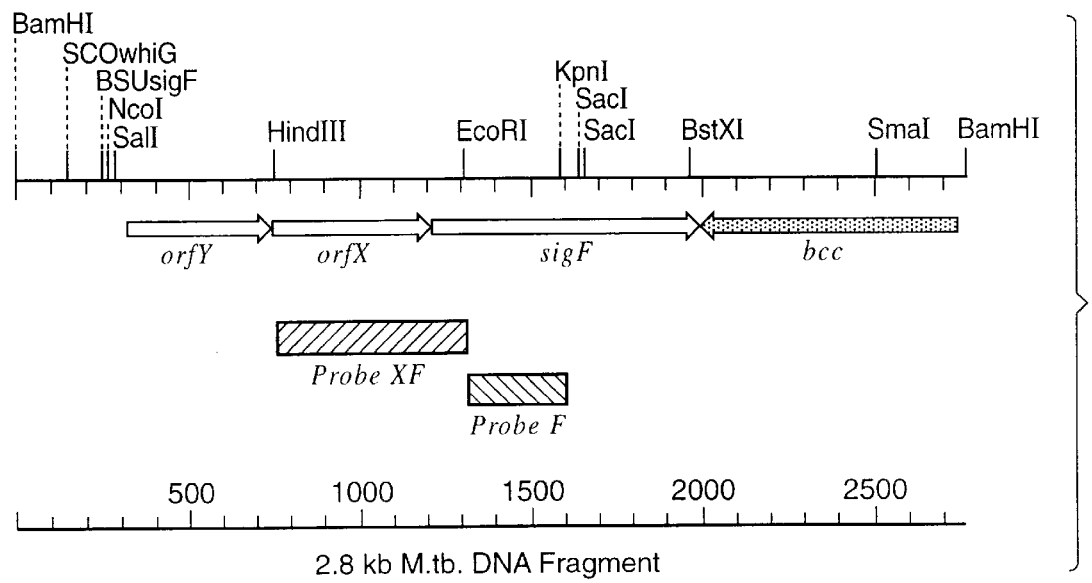
2.8 kb M.tb. DNA Fragment
FIG. IB
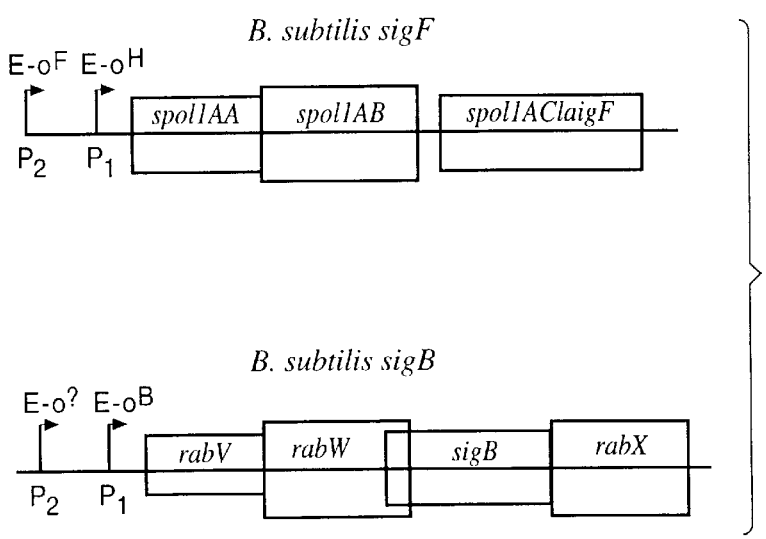

FIG. 2A

```
TCCAGACCTTCCACGACGGT CGCCAGCCCGATGTAGCCGG CAGTGTCTTCGGCATCACGT TGACCGCCCGACGGGCGGCA
                                                                              80
TCCAGCAG GTG ACG GCG CGC GCT GCC GGC GGT TCT GCA TCG CGA GCT AAC GAA TAC GCC GAC GTT
         M   T   A   R   A   A   G   G   S   A   S   R   A   N   E   Y   A   D   V>
                                                                                145/19
CCG GAG ATG TTT CGC GAG CTG GTT GGT TTG CCT GCC GGC TCA CCG GAA TTC CAG CGG CAC CGG
 P   E   M   F   R   E   L   V   G   L   P   A   G   S   P   E   F   Q   R   H   R>
                                                                              208/40
GAC AAG ATC GTT CAG CGG TGC TTG CCG CTG GCC GAT CAC ATC GCG CGG CGG TTC GAG GGT CGC
 D   K   I   V   Q   R   C   L   P   L   A   D   H   I   A   R   R   F   E   G   R>
                                                                              271/61
GGC GAA CCG CGT GAC GAC CTT ATT CAG GTC GTC CTG GGG GTC AAC GCC GCG GTT CGC
 G   E   P   R   D   D   L   I   Q   V   V   L   G   V   N   A   A   V   R>
                                                                              334/82
TTC GAC GTG AAG ACC GGG TCG GAC TTC TCC GTT GCG CCT ACC ATC ATG GGC GAG GTC
 F   D   V   K   T   G   S   D   F   S   V   A   P   T   I   M   G   E   V>
                                                                              397/103
CGA CGA CAC TTC CGC GAC AAC AGC GTC AAG GTT CCC CGG CGT CTC AAG GAA CTG CAT
 R   R   H   F   R   D   N   S   V   K   V   P   R   R   L   K   E   L   H>
                                                                              460/124
CTG CGG CTA GGT ACC GCC GAT TTG TCG CAG CGG CTC GGG CGG CCG TCG GCA TCG
 L   R   L   G   T   A   D   L   S   Q   R   L   G   R   P   S   A   S>
                                                                              523/145
```

FIG. 2B

```
GAG CTC GCC GAG CTC GGG ATG GAC CGC GCT GAG GTT ATC GAA GGT TTG CTG GCG GGT AGT      586/166
 E   L   A   E   L   G   M   D   R   A   E   V   I   E   G   L   L   A   G   S>
                                                                                    649/187
TCC TAC CAC ACC TTG TCC ATC GAC AGC GGC GGG CAG ATC GAC GAT GCC CGC GAG GTG GCA ATC ACA
 S   Y   H   T   L   S   I   D   S   G   G   Q   I   D   D   A   R   E   V   A   I   T>
                                                                                    712/208
GAC ACC CTG GGC GAC GTG GAT CCC TTG GCG GGT CTT GAC CAG ACG GAA CGA GAG AAT CGG CTT CGT CCG
 D   T   L   G   D   V   D   P   L   A   G   L   D   Q   T   E   R   E   N   R   L   R   P>
                                                                                    775/229
TTG CTC GAG GCG ATC GCC GAG CGG GAG CGC GTC TTG GTG CTC AGG TTC TTC GAC TCG ATG
 L   L   E   A   I   A   E   R   E   R   V   L   V   L   R   F   F   D   S   M>
                                                                                    838/250
ACC CAA ACG CAG CAG ATC GCC CGG GAT CAG ACG GTC ATC TCA CAG ATG CAC GTG TCG CGG CTG GCC
 T   Q   T   Q   Q   I   A   R   D   Q   T   V   I   S   Q   M   H   V   S   R   L   A>
                                  261                                              896
AAG TCA TTG GCA CGG CTA CGG GAT CAG TTG GAG TAG CCGCCGGGCTTACTTGGATCTC
 K   S   L   A   R   L   R   D   Q   L   E   *
```

FIG. 3

```
MTBSIGF   vtaraaggsasraneyadvpe---------------------------MFREL      26
SCORPOF   mpastapqappappaqaqapaqaeapaqrsgadtraltqvLFGEL              50
BSUSIGF   mdvevkknGKNAQLKDHEVKELIKQSQ-------------------------      27
BSUSIGB   mtqp----SKTTKLTKDEVDRLISDYQ---------------------------    23

MTBSIGF   VGLPAGSPEFQRHRDKIVQRCLPLADHIARRFEGRGEPRDDLIQVARVGL           76
SCORPOF   KGLAPGTPEHDRVRAALIEANLPLVRYAAARFRSRNEPMEDVVQVGTIGL          100
BSUSIGF   ------NG-DQgARDLLIEKNMRLVWSVVQRFLNRGYEPDDLFQIGCIGl           70
BSUSIGB   ------TKQDEQAQETLVRVYTNLVDMLAKKYSKGKSFHEDLRQVGMIGL           67

MTBSIGF   VNAAVRFDVKTGSDFVSFAVPTIMGEVRRHFRDNSWSVKVPRRLKELHLR          126
SCORPOF   INAIDRFDPERGVQFPTEAMPTVVGEIKRYFRDNVRTVHVPRRLHELWVQ          150
BSUSIGF   LKSVDKFDLTYDVRFSTYAVPMIIGEIQRFIRDDG-TVKVSRSLKELGNK          119
BSUSIGB   LGAIKRYDPVVGKSFEAFAIPTTIGEIKRFLRDKTWSVHVPRRIKELGPR          117

MTBSIGF   LGTATADLSQRLGRAPSASELAAELGMDRAEVIEGLLAGSSYHTLSIDSG          176
SCORPOF   VNSATEDLTTAFGRSPTTAETAERLRITEEEVLSCIEAGRSYHATSLEAA          200
BSUSIGF   IRRAKDELSKTLGRVPTVQEIADHLEIEAEDVVLAQEAVRApssihetvy          169
BSUSIGB   IKMAVDQLTETQRSPKVEELAEFLDVSEEEVLETMEMGKSYQALSVDHS           167

MTBSIGF   GGSDDDARAITDTLGDVDAGLD---QIENREVLRPLLEALPERERTVLVL          223
SCORPOF   QEGDG-LPGLLDRLGYEDP---ALDGVEHRDLVRHLLVQLPEREQRILLL          246
BSUSIGF   ---E-NDGDPITLLDQIADNSEekwf--DKIALKEAISDLEEREKLIVYL          213
BSUSIGB   IEADS-DGSTVTILDIVGSQEDGYERVNQQLMLQSVLHVLSDREKQIIDL          216

MTBSIGF   RFFDSMTQTQIAERVGISQMHVSRVLAKSLARLRDQle--------            261
SCORPOF   RYYSNLTQSQISAELGVSQMHVSRLLARSFQRLRSAnrida----            287
BSUSIGF   RYYKDQTQSEVAERLGISQVQVSRLEKKILKQIKVQmdhtdg----            255
BSUSIGB   TYIQNKSQKETGDILGISQMHVSRLQRKAVKKLREAliedpsmelm            262
```

METHOD OF IDENTIFYING COMPOUNDS THAT REGULATE THE BINDING OF *M. TUBERCULOSIS* SIGF TO *M. TUBERCULOSIS* ORFX

This is a continuation-in-part of application Ser. No. 08/622,352, filed Mar. 27, 1996, now U.S. Pat. No. 5,824,546, and application Ser. No. 08/622,353, filed Mar. 27, 1996, now U.S. Pat. No. 5,700,925.

This invention was made using U.S. government grants from the National Institutes of Health AI36973 and AI07417. Therefore the U.S. government retains certain rights to the invention.

TECHNICAL FIELD OF THE INVENTION

The present invention is directed to a gene involved in latency of infection, a diagnostic method for detecting latent *M. tuberculosis*, and methods for developing therapeutics for treating active and latent *M. tuberculosis*. The present invention is also directed to screening methods to identify agents that affect expression of a *M. tuberculosis* sigF gene or activity of a *M. tuberculosis* sigF protein.

BACKGROUND OF THE INVENTION

Tuberculosis is the leading cause of death due to infection, causing an estimated 2.5 million deaths and 7.5 million cases per year worldwide (1). In the United States, rates of tuberculosis began to increase in 1985 after 40 years of steady decline. In addition, a number of American cities are reporting high rates of infection by multiply drug resistant tuberculosis. Such mycobacteria cause a high mortality rate because available antibiotics are ineffective (2).

About 90% of individuals who become infected with *M. tuberculosis* do not have immediate symptoms but develop a positive reaction to the tuberculin skin test and carry the bacteria in a dormant or latent state (3). Over a lifetime, these individuals have a 10% risk of developing reactivation tuberculosis in which, after years of quiescence, the tubercle bacilli resume growth and cause classic pulmonary tuberculosis as well as other forms of disease. One billion people, roughly one-third of the world's population, have latent tuberculosis (4). Individuals with latent tuberculosis currently require prolonged therapy because antimycobacterial drugs work poorly against dormant bacilli.

Little is known regarding the state of dormant tubercle bacilli within the human host (5). There is a controversial body of literature describing filterable forms, granular bacillary bodies, and L-forms associated with tubercle bacilli (6, 7). These forms were reported as early as 1907 when Hans Much described granular non-acid-fast bacilli in tuberculous abscesses (30). The granules, which came to be known as Much's granules, were filterable, failed to grow in culture, and failed to produce typical tuberculosis when inoculated into animals. However, if tissue from the first animal was inoculated into a second, classic tuberculosis ensued. Similar observations have been reported over the decades for both tuberculosis (31, 32) and leprosy (33, 34). Dormant or altered mycobacterial forms have also been proposed as etiologic agents for granulomatous diseases such as sarcoidosis and inflammatory bowel disease (35). There have been reports of PCR-amplifiable, mycobacterial DNA in the tissues of patients with these diseases (36).

Because latent tubercle bacilli survive for years and cannot be detected by acid-fast staining, the bacilli must be assumed to undergo significant morphologic changes during dormancy. Though these changes are poorly understood, they could involve expression of novel mycobacterial antigens which are not produced or cannot be recovered from bacteriologic cultures grown in vitro.

There is a need in the art for diagnostic and therapeutic methods for detecting, treating, and preventing latent tuberculosis.

SUMMARY OF THE INVENTION

It is an object of the invention to provide a DNA segment encoding a *M. tuberculosis* gene.

It is an object of the invention to provide a DNA segment encoding a *M. tuberculosis* sigma factor.

It is another object of the invention to provide a preparation of an isolated sigma factor from *M. tuberculosis*.

It is another object of the invention to provide a polypeptide which consists of a portion of a sigma factor of *M. tuberculosis*.

It is still another object of the invention to provide a fusion polypeptide of an *M. tuberculosis* sigma factor.

It is another object of the invention to provide a method for detecting the presence of a latent pathogenic mycobacterium in a human.

It is still another object of the invention to provide a tuberculosis vaccine strain.

It is still another object of the invention to provide an indicator strain that measures expression and/or activity of a sigma factor of *M. tuberculosis*.

It is another object of the invention to provide a method for identifying an agent that regulates expression of a sigma factor of *M. tuberculosis*.

It is still another object of the invention to provide a method for identifying an agent that regulates activity of a sigma factor of *M. tuberculosis*.

It is another object of the invention to provide a method for identifying genes of *M. tuberculosis* which are regulated by a sigma factor of *M. tuberculosis*.

It is an object of the invention to provide a DNA segment encoding an *M. tuberculosis* protein involved in latency regulation.

It is another object of the invention to provide preparations of an isolated protein from *M. tuberculosis* which is involved in latency regulation.

It is still another object of the invention to provide a polypeptide which is the product of a genetic fusion of an *M. tuberculosis* gene involved in latency regulation.

It is still another object of the invention to provide a method for screening potential therapeutic agents for the ability to trigger or inhibit the growth arrest of *M. tuberculosis*.

It is another object of the invention to provide a reporter construct for screening potential therapeutic agents.

It is yet another object of the invention to provide a method for screening potential therapeutic agents for use in regulating the growth of *M. tuberculosis*.

It is still another object of the invention to provide a method of identifying compounds which regulate the binding of two *M. tuberculosis* proteins involved in latency.

These and other objects of the invention are provided by one or more of the embodiments described below.

In one embodiment of the invention an isolated and purified subgenomic DNA segment is provided. Its nucleotide sequence is shown in SEQ ID NO:1.

In a first embodiment of the invention an isolated and purified subgenomic DNA segment encoding an *M. tuber-*

*culosis* sigma factor sigF as shown in SEQ ID NO:2 is provided. In another embodiment of the invention a preparation of an isolated sigma factor sigF from *M. tuberculosis* is provided. The amino acid sequence of the sigma factor is shown in SEQ ID NO:2.

In yet another embodiment of the invention a preparation which consists of a polypeptide is provided. The polypeptide is a sigma factor sigF from *M. tuberculosis* as shown in SEQ ID NO:2.

In another embodiment of the invention a preparation of an isolated polypeptide is provided which consists of at least four contiguous amino acids of the sequence shown in SEQ ID NO:2.

In still another embodiment of the invention a fusion polypeptide is provided. The polypeptide is the product of a genetic fusion of a first and second gene sequence, wherein the first sequence is an *M. tuberculosis* sigF gene and the second sequence encodes all or a portion of a second protein.

In another embodiment of the invention a method is provided of detecting the presence of a latent pathogenic mycobacterium in a human. The method comprises the steps of: detecting sigma factor sigF in a body sample isolated from a human, the presence of sigma factor sigF indicating a latent pathogenic mycobacterial infection in a human.

In still another embodiment of the invention a tuberculosis vaccine is provided which comprises an *M. tuberculosis* strain with a mutation disrupting the reading frame of its sigF gene.

In still another embodiment of the invention an indicator strain is provided that measures expression and/or activity of a sigma factor of *M. tuberculosis*.

In another embodiment of the invention a method is provided of identifying an agent that regulates expression of a sigma factor of *M. tuberculosis*.

In still another embodiment of the invention a method is provided of identifying an agent that regulates activity of a sigma factor of *M. tuberculosis*.

In another embodiment of the invention a method is provided of identifying a gene or a protein which is regulated by a sigma factor of *M. tuberculosis*.

In a second embodiment of the invention an isolated and purified subgenomic DNA segment encoding an *M. tuberculosis* orfX is provided.

In another embodiment of the invention a preparation of an isolated orfX from *M. tuberculosis* is provided.

In yet another embodiment of the invention a preparation is provided which consists of an orfX polypeptide from *M. tuberculosis*.

In another embodiment of the invention a preparation is provided which consists of a polypeptide consisting of at least four contiguous amino acids of the sequence shown in SEQ ID NO:3.

In still another embodiment of the invention a polypeptide is provided. The polypeptide is the product of a genetic fusion of a first and second gene sequence, wherein the first sequence is all or a portion of an *M. tuberculosis* orfX gene and the second sequence encodes all or a portion of a second protein.

In a third embodiment of the invention an isolated and purified subgenomic DNA segment encoding an *M. tuberculosis* orfY is provided.

In another embodiment of the invention a preparation of an isolated orfY from *M. tuberculosis* is provided.

In yet another embodiment of the invention a preparation is provided which consists of an orfY polypeptide from *M. tuberculosis*.

In another embodiment of the invention a preparation is provided which consists of a polypeptide consisting of at least four contiguous amino acids of the sequence shown in SEQ ID NO:4.

In still another embodiment of the invention a polypeptide is provided. The polypeptide is the product of a genetic fusion of a first and second gene sequence, wherein the first sequence is all or a portion of a *M. tuberculosis* orfY gene and the second sequence encodes all or a portion of a second protein.

In yet another embodiment of the invention a reporter construct is provided. The reporter comprises a sigF transcription regulatory region covalently linked in a cis configuration 5' of a gene encoding an assayable product, wherein transcription of the gene is regulated by the sigF transcription regulatory region.

In another embodiment of the invention a method is provided for screening potential therapeutic agents for the ability to trigger the growth arrest of *M. tuberculosis* by activating the expression of sigF, or to reactivate latent *M. tuberculosis* by inhibiting the expression of sigF. The method comprises the steps of: incubating a potential therapeutic agent with a cell which contains a sigF reporter construct, said reporter construct comprising a sigF transcription regulatory region covalently linked in a cis configuration to a downstream gene encoding an assayable product; and measuring the production of the assayable product, a potential therapeutic agent which increases the production by the cell of the assayable product being an agent which will trigger the growth arrest of *M. tuberculosis* by activating the expression of sigF, and a potential therapeutic agent which decreases the production by the cell of the assayable product being an agent which will reactivate *M. tuberculosis* by inhibiting the expression of sigF.

In still another embodiment of the invention a method is provided for screening potential therapeutic agents for use in modulating the growth of *M. tuberculosis* by regulating the activity of *M. tuberculosis* sigF. The method comprises the steps of: measuring in vitro transcription from the transcription construct incubated with *M. tuberculosis* sigF in the presence or absence of a test compound, the transcription construct comprising a gene coding sequence and a promoter which is responsive to *M. tuberculosis* sigF, the promoter being upstream from and adjacent to the gene, the in vitro transcription being effected in the presence and absence of a test substance; and determining whether transcription of the gene is altered by the presence of said test substance, a test substance which alters the transcription of the gene being a candidate for use in regulating the growth of *M. tuberculosis*.

In yet another embodiment of the invention a method of identifying compounds which regulate the binding of *M. tuberculosis* sigF protein to orfX protein is provided. The method comprises the steps of: incubating *M. tuberculosis* sigF protein immobilized on a solid support with a test compound and *M. tuberculosis* orfX; and determining the amount of the *M. tuberculosis* orfX protein which is bound to the *M. tuberculosis* sigF protein, a desirable test compound being one which increases or decreases binding of the *M. tuberculosis* orfX protein to *M. tuberculosis* sigF protein. The method may also comprise the steps of: incubating *M. tuberculosis* orfX protein immobilized on a solid support with a test compound and *M. tuberculosis* sigF protein; and determining the amount of the *M. tuberculosis* sigF protein which is bound to the *M. tuberculosis* orfX protein, a desirable test compound being one which increases or decreases binding of the *M. tuberculosis* sigF protein to *M. tuberculosis* orfX protein.

These and other embodiments of the invention provide the art with diagnostic, therapeutic and prophylactic reagents and methods for combatting latent tuberculosis, and reagents and methods for identifying therapeutic agents to treat active and latent tuberculosis.

BRIEF DESCRIPTION OF THE DRAWINGS

FIGS. 1A–1B. Map of 2.8 kb *M. tuberculosis* DNA fragment containing sigF.

FIG. 1A shows the restriction map and open reading frame analysis of the *M. tuberculosis* sigF gene cluster. The relative positions of restriction sites, the sigF open-reading frame, and the positions of promoter consensus sites for *Streptomyces coelicolor* WhiG (SCOwhiG) and *Bacillus subtilis* SigF (BSUsigF) are shown. Numbers along the bottom line are in base pairs (bp).

FIG. 1B shows the genetic organization of the *B. subtilis* sigF and *B. subtilis* sigB gene clusters for comparison. Diagram shows that the arrangement anti-anti-sigma→anti-sigma→sigma is conserved since spoIIAA and rsbV encode anti-anti-sigmas, and spoIIAB and rsbW encode anti-sigmas.

FIGS. 2A–2B. DNA and deduced protein sequence of the *M. tuberculosis* sigF region.

Figure 4:
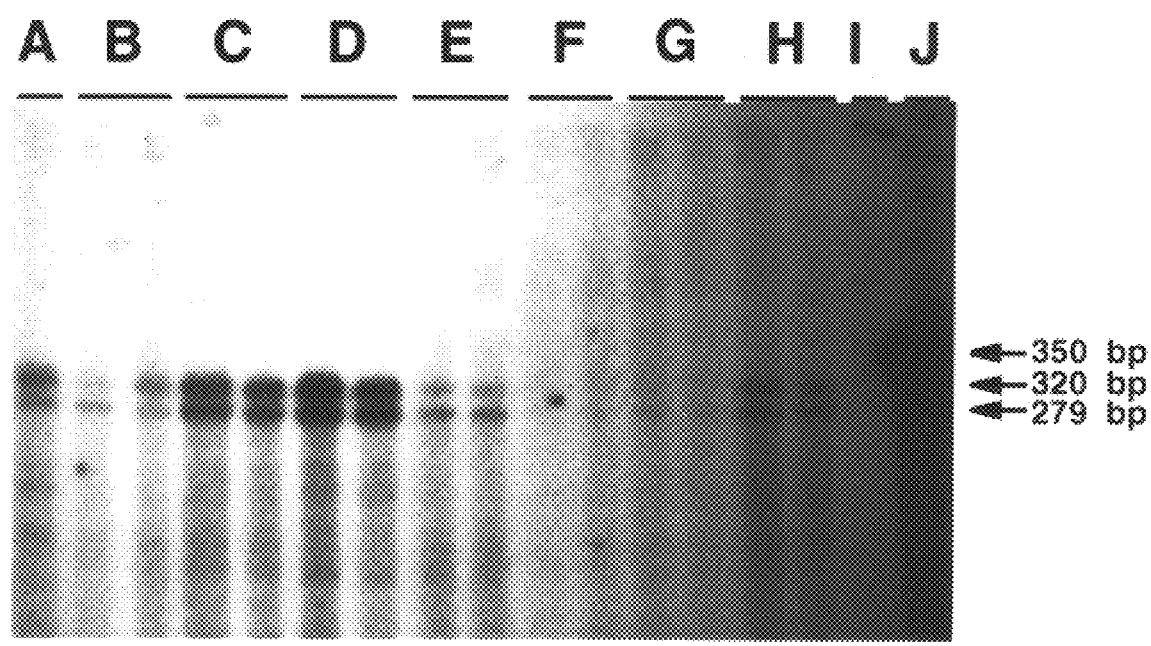

The 896 bp of *M. tuberculosis* DNA sequenced (bases 1094–1989 of SEQ ID NO:1 is shown along with the deduced protein sequence of sigF (SEQ ID NO:2). Numbers at right correspond to nucleotide or amino acid positions.

FIG. 3. Alignment of *M. tuberculosis* sigF with related sigma factors.

The deduced amino acid sequences of *M. tuberculosis* sigF aligned with homologs using the MACAW algorithm (29). Capitalized blocks of amino acids represent segments with statistically significant homology scores. Black and gray shading indicates amino acid similarity (black being the highest). The length of each polypeptide is shown by the numbers on the right. BSUSIGF=*Bacillus subtilis* sigF (Acc. No. M15744, SEQ ID NO:10), BSUSIGB=*Bacillus subtilis* SigB (Acc. No. M13927, SEQ ID NO:1), and SCORPOF=*Streptomyces coelicolor* sigF (Acc. No. L11648, SEQ ID NO:9).

FIG. 4. RNase protection assay (RPA) with RNA extracts from *M. bovis* BCG exposed to different conditions.

Autoradiogram of RPA reaction products following liquid hybridization between total *M. bovis* BCG RNA and the pCK1845-derived sigF-specific antisense RNA probe separated on a 5% denaturing polyacrylamide gel and exposed to X-ray film for 24 hr. Samples B–H were assayed in duplicate. RPA was performed upon equivalent amounts of total RNA from *M. bovis* BCG cultures subjected to the following conditions: A, 10 mM $H_2O_2$; B, 5% EtOH; C, nitrogen depletion; D, cold shock; E, microaerophilic stress; F, early exponential growth ($A_{600}$=0.67); G, late exponential growth ($A_{600}$=1.5); H, stationary phase ($A_{600}$=2.7). Control samples were: I, an in vitro transcribed non-complementary probe (negative control); J, in vitro transcribed sense-strand sigF probe containing 350 complementary bases (positive control).

DETAILED DESCRIPTION OF THE INVENTION

It is a discovery of the present invention that entry of *M. tuberculosis* into a latent state is under the influence of an *M. tuberculosis* gene encoding a sigma factor, sigF. The expression of *M. tuberculosis* gene sigF indicates the latent state of *M. tuberculosis*.

It is another discovery of the present invention that *M. tuberculosis* sigF is regulated by *M. tuberculosis* orfX and orfY proteins. The *M. tuberculosis* sigF protein by itself or in combination with *M. tuberculosis* orfX and orfY can be used to screen for dormancy inducers which function as bacteriostatic antibiotics by triggering growth cessation during active tuberculosis infection. They can also be used to screen for antagonists useful as reactivation inducers to stimulate controlled reactivation in patients with latent tuberculosis. Reactivation will render antimycobacterial drugs more effective, because the drugs are typically more potent toward actively growing bacilli.

An *M. tuberculosis* sigF DNA segment can be isolated by amplifying sigma-like gene fragments from *M. tuberculosis* genomic DNA using polymerase chain reaction with degenerate primers. Primers are designed to anneal to conserved regions of bacterial sigma factors. PCR fragments which are generated are subsequently used to screen an *M. tuberculosis* genomic library. The clones which hybridize to the PCR fragments are analyzed by standard sequencing methods. This sequence data was to sigma factors from other species, e.g., *M. smegmatis*, and clones which show strong homology to sigma factors previously described from other mycobacteria are further analyzed. The sequence of one such genomic clone is 2.8 kb. As shown in SEQ ID NO:1, the clone contains the *M. tuberculosis* sigma factor sigF *M. tuberculosis* orfX, and *M. tuberculosis* orfY genes.

The sequence of the clone reveals a 261 codon open-reading frame (nucleotides 1182–1964 in SEQ ID NO:1) encoding *M. tuberculosis* sigF protein as shown in SEQ ID NO:2.

The sequence also reveals an open-reading frame encoding *M. tuberculosis* orfX protein. The open-reading frame is 242 codons (nucleotides 457–1182 in SEQ ID NO:1, amino acids 1 to 242 in SEQ ID NO:3), 208 codons (nucleotides 559–1182 in SEQ ID NO:1, amino acids 35 to 242 in SEQ ID NO:3), 168 codons (nucleotides 679–1182 in SEQ ID NO:1, amino acids 75 to 242 in SEQ ID NO:3), or 145 codons (nucleotides 748–1182 in SEQ ID NO:1, amino acids 98 to 242 in SEQ ID NO:3) depending on which start codon is used. Analysis of codon usage suggests that the 145 codon product is synthesized.

Similarly, the sequence reveals an open-reading frame encoding *M. tuberculosis* orfY protein. The open-reading frame is 137 codons (nucleotides 137–547 in SEQ ID NO:1, amino acids 1 to 137 in SEQ ID NO:4), 122 codons (nucleotides 182–547 in SEQ ID NO:1, amino acids 16 to 137 in SEQ ID NO:4), 120 codons (nucleotides 188–547 in SEQ ID NO:1, amino acids 18 to 137 in SEQ ID NO:4), or 103 codons (nucleotides 239–547 in SEQ ID NO:1, amino acids 35 to 137 in SEQ ID NO:4) depending on which start codon is used. Analysis of codon usage suggests that the 103 codon product is synthesized.

Either one or more start codons may be used physiologically, for both orfX and orfY. It is well within the ability of a person skilled in the art to determine which start codon is used physiologically. For example, antibody can be generated against a C-terminal domain and the molecular weight of the polypeptide may then be determined by Western blot, or the N-terminal sequence of purified polypeptide can be determined by Edman degradation. Alternatively, constructs employing different start codons can be expressed to produce polypeptides which can be tested for their ability to interact with sigF.

A subgenomic DNA segment consisting of the nucleotide sequence shown in SEQ ID NO:1, or encoding an *M. tuberculosis* sigF protein (SEQ ID NO:2), orfX protein (SEQ ID NO:3), or orfY protein (SEQ ID NO:4) can be readily isolated and purified from a recombinant clone, or directly from *M. tuberculosis* DNA or RNA. Any known methods for subgenomic DNA segment isolation (e.g., nucleic acid amplification or restriction enzyme digestion) can be used employing the sequence information disclosed in SEQ ID NO:1.

The DNA sequence provided herein can be used to form vectors which will replicate the sigF, orfX, or orfY gene in a host cell.

Vectors may comprise an expression control sequence and preferably express all or a part, of the *M. tuberculosis* sigF protein. Suitable vectors, for expression of proteins in both prokaryotic and eukaryotic cells, are known in the art. Some vectors are specifically designed to effect expression of inserted DNA segments downstream from a transcriptional and translational control site. Selection of a vector for a particular purpose may be made using knowledge of the properties and features of the vectors, such as useful expression control sequences. Vectors can be used to transform host cells. Methods of transformation are known in the art, and can be used according to suitability for a particular host cell. Host cells can be selected according to their known characteristics. Non-mycobacterial cells are particularly desirable.

DNA sequences which encode the same amino acid sequence as shown in SEQ ID NOS:2–4 can also be used (e.g., for expressing sigF, orfX, or orfY) without departing from the contemplated invention. Such sequences can be readily designed using the genetic code and its inherent degeneracy. Variations from the sequence shown in SEQ ID NO:1 can be made, as is known in the art, employing alternate codon for the same amino acids, or employing alternate sequences in the non-coding region.

A portion or all of the *M. tuberculosis* sigF, orfX, or orfY gene can also be cloned in-frame with a second protein-coding sequence to make a fusion protein. A portion of the desired gene can encode at least four, six, eight, twelve or fifteen contiguous amino acids of the desired protein. Such polypeptides are useful as immunogens or as competitive antigens. It may be desirable to separate the desired protein from the second protein with a peptide recognition site for a proteolytic enzyme (e.g., enterokinase, thrombin, factor Xa, subtilisin). Preferably the contiguous amino acids of the desired protein form an immunogen or epitope, or another functional domain.

The second protein-coding sequence of the fusion protein may be all or a portion of a protein, e.g., a secretion or targeting signal, glutathione-S-transferase (GST), hexahistidine, maltose binding protein (malE), β-galactosidase (lacZ), FLAG peptide, 9E10-myc epitope, or hemagglutinin (HA). The fusion protein preferably is immunogenic and enhances the immune response to sigF, orfX, or orfY protein; delivers the fusion protein to a particular site in the cell or body; or facilitates protein purification.

The second protein-coding sequence may encode at least four, six, eight, twelve or fifteen contiguous amino acids of the second protein; or a functional domain of the second protein. The product of the genetic fusion of the *M. tuberculosis* sigF, orfX, or orfY gene and the second protein-encoding sequence is may be used to generate antibodies specifically immunoreactive to *M. tuberculosis* sigF, orfX, or orfY protein; or as an affinity matrix to identify interacting proteins from a mixture.

The sigF, orfX, or orfY protein can be isolated from *M. tuberculosis* by any means known in the art for purifying proteins. For example, antibodies which specifically bind to the protein (see discussion below) can be employed for affinity purification. The procedures for protein purification are well known and routinely practiced in the art (e.g., precipitation, electrophoresis, chromatography). Proteins or polypeptides can be prepared and isolated substantially free of other mycobacterial proteins inter alia from transformed non-mycobacterial host cells expressing the protein or the polypeptide.

Clinical specimens can be tested for the presence of a dormant pathogenic mycobacterium including *M. tuberculosis*. The presence of *M. tuberculosis* sigF in a body sample indicates a latent pathogenic mycobacterial infection in a human. The clinical specimens can include samples obtained from biopsies, blood, and body discharge such as sputum, gastric content, spinal fluid, urine, and the like. Mycobacterial RNA or protein of the specimen may be isolated directly from the specimen using any procedure known in the art. Example 3 shows that the presence of sigF homologs appears to be unique to slow-growing mycobacteria, and largely restricted to those which are intracellular pathogens.

The presence of *M. tuberculosis* sigF, orfX, or orfY RNA may be detected by Northern blot, RNAse protection assay, primer extension, RT-PCR, or any other method known in the art. The probes and primers used in these methods can be designed based on the sequence disclosed in SEQ ID NO:1; this is well within the ability of persons of ordinary skill in the art. The probes for Northern blot and RNAse protection assay may be at least 20, 40, or 60 base pairs in length, preferably about 100 to 200 base pairs. The primers for RT-PCR and primer extension may be at least 10 base pairs in length and preferably about 20 base pairs. The probes and primers should be unique to the *M. tuberculosis* sigF, orfX, or orfY gene.

The presence of *M. tuberculosis* sigF, orfX, or orfY protein can be detected by Western blot, sandwich assay, immunoprecipitation, or any other techniques known in the art. Monoclonal or polyclonal antibodies raised using *M. tuberculosis* sigF, orfX, or orfY protein or polypeptides as an immunogen can be used as probes in Western blot, can be bound to a solid support phase for sandwich assay, or can be used to immunoprecipitate radioactively labelled *M. tuberculosis* sigF, orfX, or orfY protein.

An antibody preparation which is specifically immunoreactive with *M. tuberculosis* sigF, orfX, or orfY protein can be obtained by standard techniques known in the art. Briefly, animals can be immunized with peptides along with adjuvants to generate polyclonal antibodies or hybridomas can be generated to obtain monoclonal antibodies. Antibodies may be polyclonal or monoclonal and may be raised using any protein containing epitopes of the desired protein as an immunogen, including native protein, fusion protein, or synthetic peptides. The antibodies should be specifically immunoreactive with a sigF, orfX, or orfY epitope. Preferably the selected epitopes will not be present on other mycobacterial or human proteins.

Though not wishing to be limited to any particular mechanism of action, it is postulated that *M. tuberculosis* orfX and orfY protein regulate sigF through the same mechanism employed by the SigF and SigB families in *B. subtilis*. The mechanism used in *B. subtilis* is a "partner-switching"

mechanism between sigma factor, anti-sigma factor, and anti-anti-sigma factor. *B. subtilis* SigF is regulated by anti-sigma factor SpoIIAB and anti-anti-sigma factor SpoIIAA, the genes for both of which are co-transcribed with the SigF gene. *B. subtilis* SigB is activated by stress and starvation and controls a large regulon of stress response genes. Similarly, SigB is controlled by anti-sigma factor RsbW and an anti-anti-sigma factor RsbV, the genes for both of which are also co-transcribed with the SigB gene. Importantly, the arrangement of genes in the polycistronic messages for *B. subtilis* SigF family and SigB family is the same: anti-anti-sigma factor, anti-sigma factor, sigma factor as illustrated in FIG. 1B.

*M. tuberculosis* sigF, *B. subtilis* SigF and SigB protein have strong similarities to each other based on the database searches for protein homologs. An alignment of *M. tuberculosis* sigF, *B. subtilis* SigF and SigB proteins is shown in FIG. 3. Even though anti-sigma factors are a divergent family of protein kinases, RsbW shares 16% amino acid identity with orfX and SpoIIAB shares 13% identity with orfX. An alignment of these proteins reveals two blocks of homology which are common to a larger family of bacterial protein kinases (27). Therefore in the *M. tuberculosis* sigF family, it is believed that orfX is an anti-sigma factor, and orfY is an anti-anti-sigma factor. Anti-sigma factors sequester sigma factors to negatively regulate the function of the sigma factors. The anti-sigma factor may switch to bind the anti-anti-sigma factor thereby releasing the inhibition.

Based on the present discoveries, screening methods have been devised to identify chemical agents which have use in therapy for treating active and latent tuberculosis. Potential therapeutic agents can be screened for the ability to activate or inhibit the expression of *M. tuberculosis* sigF gene. According to one method, the ability of a test substance or a potential therapeutic agent to activate or inhibit the expression of *M. tuberculosis* sigF gene is assessed by measuring the activity of a reporter construct in a cell. A reporter construct comprises a reporter gene, i.e. a gene encoding a conveniently assayable enzyme activity, such as chloramphenicol acetyltransferase or β-galactosidase, and a transcriptional regulatory region of *M. tuberculosis* sigF as shown in SEQ ID NO:1.

The transcriptional regulatory region of *M. tuberculosis* sigF gene may comprise the sequence of nucleotides 1 to 1245 of SEQ ID NO:1. It may contain at least the sequence of nucleotides 1045 to 1245, 845 to 1245, 645 to 1245, 445 to 1245, or 245 to 1245 of SEQ ID NO:1. It may alternatively or additionally contain at least the sequence of nucleotides 1 to 245, 1 to 445, 1 to 645, 1 to 845, or 1 to 1045 of SEQ ID NO:1. It may alternatively or additionally also contain the sequence of nucleotides 1 to 200, 200 to 400, 400 to 600, 600 to 800, 800 to 1000, and 1000 to 1245. The reporter genes are covalently linked in a cis configuration with the regulatory region 5' of the reporter gene. Alternatively, the transcriptional region of *M. tuberculosis* sigF gene may contain part of the coding region of the sigF gene (e.g., nucleotides 1 to 1280 of SEQ ID NO:1) and may be fused in-frame with the reporter gene.

Methods for measuring transcriptional or translational activity in vivo can be any which are known in the art. For example, a nuclear run on assay may be employed to measure the transcription of the reporter gene. The translation of the reporter gene may be measured by determining the activity of the translation product of the reporter gene. Methods for measuring the activity of an assayable product of certain reporter genes are well known in the art.

In a preferred embodiment, the assayable product is measured in mycobacteria growing in rich medium when sigF activity is expected to be low. In another preferred embodiment, the assayable product is measured in mycobacteria in a stressed condition, e.g., nitrogen starvation, when sigF activity is expected to be high.

Potential therapeutic agents can also be screened for use in regulating the growth of *M. tuberculosis* by their ability to regulate the activity of *M. tuberculosis* sigF protein. The ability of a test compound or a potential therapeutic agent to regulate the activity of *M. tuberculosis* sigF protein is assessed by measuring the transcription of a promoter in an in vitro transcription assay.

A transcription reaction comprises a promoter responsive to *M. tuberculosis* sigF protein and a gene. The gene in the transcription construct could be any gene known in the art. In a preferred embodiment, the length of the promoter region to be tested is less than 200 bp and no more than 600 bp. The promoter in the transcription construct can be any to which *M. tuberculosis* sigF protein binds and which it activates. The promoter is responsive to *M. tuberculosis* sigF protein which induces the transcription of the gene downstream from and adjacent to the promoter. One such promoter comprises the sequence of nucleotides 1 to 350 in SEQ ID NO:1. Other candidate promoters may be identified as consensus promoter sequences (37).

Suitable methods for measuring in vitro transcription are any known in the art. In vitro transcription may be carried out by incubating a transcription construct with *M. tuberculosis* sigF protein, labeled nucleotides, e.g., $^{32}$P-ATP, core RNA polymerase, nucleotides, and buffer reagents in the presence and absence of a test compound (44). The procedures for purifying core RNA polymerase from mycobacteria are well-described in the art (45). The conditions for in vitro transcription are also well known in the art (46). The labeled transcript can be detected by gel electrophoresis and measured by any technique known in the art. Optionally, in vitro transcription can be carried out in the presence of *M. tuberculosis* orfX protein or both *M. tuberculosis* orfX and orfY protein.

A potential therapeutic agent which increases the production of the assayable product in the cell indicates its ability to increase the expression of *M. tuberculosis* sigF. A potential therapeutic agent which increases the level of in vitro transcription indicates its ability to enhance the activity of the transcriptional activating *M. tuberculosis* sigF protein. Test compounds which increase the expression of *M. tuberculosis* sigF gene or the activity of the sigF protein can trigger the growth arrest of *M. tuberculosis*. These compounds can be administered to a human with active tuberculosis, especially those who respond poorly to conventional antibiotic treatments. These compounds can induce growth arrest of *M. tuberculosis*, and initiate dormancy during severely advanced progressive tuberculosis or multi-drug resistant tuberculosis.

A test substance which decreases the production of the assayable product in the cell indicates its ability to decrease the expression of *M. tuberculosis* sigF. A test substance which decreases the level of in vitro transcription indicates its ability to inhibit the activity of the *M. tuberculosis* sigF protein. Test compounds which decrease the expression of *M. tuberculosis* sigF or the activity of the sigF protein can reactivate latent *M. tuberculosis*. These compounds can be used in the treatment of active tuberculosis to neutralize the sigF protein and prevent mycobacterial adaptation so that mycobacteria can not make the changes necessary to evade the host immune system and enter an antibiotic-insensitive latent state. These compounds can also be used in the treatment of latent tuberculosis to neutralize the sigF protein and force the mycobacteria to reactivate in a controlled fashion so that they may be inhibited and/or killed quickly and efficiently using antibiotics. The compound and the antibiotic can be administered either (a) simultaneously (optionally by formulating the two together in a common carrier), or (b) at different times during the course of a common treatment schedule. In the latter case, the two compounds are administered at times sufficiently close for the antibiotic to efficiently kill or inhibit the growth of the reactivated M. tuberculosis. This may be within one month, one week, one day or one hour.

According to another embodiment of the invention, compounds regulating the binding between M. tuberculosis sigF protein and orfX protein may be identified. M. tuberculosis sigF protein can be attached to an insoluble polymeric support such as agarose, cellulose, or the like. A test compound is incubated with the immobilized sigF protein in the presence of M. tuberculosis orfX protein or both orfY and orfX protein. Alternatively, orfX protein can be immobilized on a solid support and a test compound can be incubated with the immobilized orfX protein in the presence of M. tuberculosis sigF protein or both sigF and orfY protein. The conditions for binding among anti-sigma factor, sigma factor, and anti-anti-sigma factor are well characterized and known in the art. Particularly, Alper et al. (28) describes the binding conditions for SpoIIAA, SpoIIAB, and sigma factor. After incubation, all non-binding components can be washed away, leaving orfX protein bound to the sigF protein/solid support or sigF protein bound to the orfX protein/solid support. The amount of orfX or sigF can be quantified by any means known in the art. For example, it can be determined using an immunological assay, such as ELISA, RIA, or Western blotting. The amount of bound orfX or sigF is determined with and without the test compound. A desirable compound is one which increases or decreases the binding of orfX protein to M. tuberculosis sigF protein in the presence or absence of orfY protein.

An M. tuberculosis strain can be constructed with a mutation, preferably one which disrupts the reading frame of the sigF gene. The mutation can be a deletion of part or all of a sigF gene. The sigF gene can also be disrupted by insertion or substitution mutations. Frame shift and nonsense mutations can also be employed. These mutations can be made by any means known in the art, e.g., PCR, restriction digestion, in vitro or in vivo mutagenesis. Such a strain with a dysfunctional sigF gene grows actively within a mammalian host for several weeks inducing a strong immune response, but because of the absence of a functional sigF protein, it is unable to establish a persistent infection. The host immune system is therefore able to clear the infection. Such a sigF mutant strain may be useful as an anti-tuberculosis vaccine.

The site of action of the antibiotic rifampicin is bacterial transcription. Targeting transcription as a step in the bacterial adaptive response has not yet been exploited in drug screening programs, but such a program has the potential to identify new drugs. Agents to manipulate adaptive responses are needed for organisms like Mycobacteria which enter slow-growing, resistant states as part of their adaptive response. sigF activators may act as latency activators which inhibit active tuberculosis, while sigF blockers may act as latency inhibitors which block latency adaptation and potentiate the activity of anti-mycobacterial drugs already available.

The identification of sigF-dependent genes and proteins will provide additional targets for drug development. Mycobacteria (e.g., M. smegmatis, M. bovis BCG, or M. tuberculosis) cultures may be compared prior to and after induction of sigF. Transcription of sigF-dependent genes may be activated by culture or stress conditions which induce sigF, or by introducing the sigF gene under the control of an inducible promoter into a host cell that lacks endogenous sigF. sigF-dependent genes may be identified by screening a subtractive cDNA library (e.g., post-induction transcripts minus pre-induction transcripts), or by differential screening of cDNA or genomic clone libraries. The sigF-dependent transcripts will be translated into sigF-dependent proteins, such proteins may be identified by comparing the pattern of proteins expressed prior to and after induction of sigF. For example, pre- and post-induction cultures of mycobacteria may be $^{35}$S-pulsed, protein extracts may be made from whole cell lysates or subcellular fractions, and sigF-dependent proteins will be identified by their increased or decreased signal intensity in two-dimensional gels of $^{35}$S-labeled proteins from pre- and post-induction cultures. Proteins of interest (i.e., labeled proteins which increase or decrease in abundance) may be isolated, N-terminal or internal peptide amino acid sequence may be determined, and the sigF-dependent gene of interest identified.

sigF-dependent genes may also be identified by promoter trapping. sigF may be induced in M. tuberculosis by culture or stress conditions, or by introducing the sigF gene under the control of an inducible promoter into a host cell that lacks endogenous sigF. A clone library of M. tuberculosis genomic DNA fragments inserted into a promoter probe vector (the general strategy used in making such vectors for E. coli and B. subtilis hosts is described in U.S. Pat. No. 4,725,535, incorporated herein by reference) can be constructed to operably link the DNA fragment with an indicator gene (e.g., lacZ, luxAB, xlyE, firefly luciferase, the gene for green fluorescent protein or gfp, melC), such that a promoter contained in the DNA fragment may direct the transcription of the indicator gene. A suitable indicator gene will be transcribed and produce a detectable indicator product under appropriate assay conditions. Individual clones of the library may be introduced into M. tuberculosis or the host cell, and colonies replica plated under conditions of sigF induction or noninduction. DNA fragments will be isolated from colonies which produce indicator product only when sigF is induced because they could contain sigF-dependent promoters. Alternatively, a construct containing the indicator gene but no operably linked promoter may be randomly integrated into the chromosome of M. tuberculosis. Clones which contain integrations near sigF-dependent promoters may be identified after induction of sigF by screening for the indicator product. Those integrations could mark the sites of sigF-dependent promoters and isolating the M. tuberculosis genes associated with such promoters may also identify sigF-dependent genes.

The following examples are provided for exemplification purposes only and are not intended to limit the scope of the invention.

EXAMPLE 1

PCR with degenerate sigma-70 consensus primers successfully identifies an M. tuberculosis sigma factor gene, sigF Degenerate primers Y207 (5'-AACCTGCGHC-TSGTSGTC-3', SEQ ID NO:5, forward primer for hexapeptide NLRLVV, SEQ ID NO:6) and Y208 (5'-CTGNCGKATCCACCASGTSGCRTA-3', SEQ ID NO:7, reverse primer for octapeptide YATWWIRQ, SEQ ID NO:8) were used to amplify sigma factor gene fragments from M.

tuberculosis genomic DNA in standard PCR reactions with Taq polymerase (Gibco-BRL, Gaithersburg, Md.): 30 cycles, 94° C. for 60 sec, 54° C. for 90 sec, and 72° C. for 120 sec. PCR products were cloned and used as probes to select genomic clones from an *M. tuberculosis* H37Rv cosmid library. Analysis of bacterial sigma factors reveals considerable conservation in regions 2.1–2.4 and 4.1–4.2 (11). Region 2.1 is implicated in core polymerase-binding while the 2.3/2.4 and 4.2 regions are believed to contact the −10 and −35 regions, respectively, of the promoter DNA consensus sequence (12). We designed degenerate primers Y207 and Y208 directed towards conserved regions 2.1 and 2.3, respectively, and used them to amplify sigma-like gene fragments from *M. tuberculosis* genomic DNA. These primers amplified several distinct products including the anticipated 165 bp fragment. This 165 fragment was likely to consist of a mixture of sequences since it hybridized strongly to two separate *M. tuberculosis* BamHI fragments (4.8 kb and 2.8 kb) by Southern analysis. *E. coli* cosmid clones which hybridized with the 165 bp PCR product were selected by screening an *M. tuberculosis* H37Rv library, and the 2.8 kb BamHI fragment was subcloned as pYZ99 from one of these cosmids. A restriction map of the 2.8 kb BamHI fragment is shown in FIG. 1. The 4.8 kb BamHI fragment appears to be identical to a 7 kb fragment from *M. tuberculosis* which has been sequenced (S. Cole and I. Smith, personal communication). This fragment also showed strong homology to one of the sigma factors previously described from *M. smegmatis* (13).

Sigma factors are subunits of bacterial RNA polymerase and confer promoter specificity to the holoenzyme complex. The unique affinity of each sigma factor for its promoter consensus sequence is an essential component in many gene regulation systems. For example, in *Bacillus subtilis*, sporulation is regulated by a carefully-coordinated cascade of alternate sigma factors and the genes which they control (37).

The structure and function of sigma factors are conserved across species, and these regions of conservation may be exploited to identify new sigma factors (16). We successfully employed PCR using degenerate primers based on conserved regions 2.1 and 2.3 to identify a new *M. tuberculosis* sigma factor gene, sigF.

EXAMPLE 2

The sequence of the *M. tuberculosis* sigma factor gene, sigF

DNA sequencing was performed with an Applied Biosystems 373 automated DNA sequencer (Foster City, Calif.) using dye terminator chemistry at the Biopolymer lab of the Howard Hughes Medical Institute at The Johns Hopkins University School of Medicine.

A combination of primer walking and subcloning of restriction fragments was used to determine the DNA sequence of 896 bp of pYZ99 which contains the sigma factor gene, sigF as shown in FIGS. 2A–B. Each base was sequenced an average of 5 times (minimum 3, maximum 8). The sequence reveals a 261 amino acid open-reading frame. The 88 bp of upstream sequence does not contain significant homology to *E. coli* sigma-70 promoter consensus sequences, nor does it have a clear-cut Shine-Dalgarno ribosome binding site with complementarity to the 3' end of the *M. tuberculosis* 16S rRNA sequence (14). Nevertheless, the sigF gene is clearly transcribed in slow-growing mycobacteria (see below). Our assignment of the initiation codon is based on alignments with other known sigF-like proteins (see below) and the observation that GTG is commonly used as an initiation codon in mycobacteria (15).

EXAMPLE 3

Homologs of sigF

The 261 aa deduced protein encoded by *M. tuberculosis* sigF has significant homology to the known stress and sporulation-specific sigma factors from Bacillus spp. and Streptomyces spp. The closest similarities are to *S. coelicolor* SigF (41% identity and 62% similarity), *B. subtilis* SigB (30% identity and 50% similarity) and *B. subtilis* SigF (26% identity and 44% similarity). An alignment of the deduced *M. tuberculosis* sigF protein sequence with these three other sigma factors is shown in FIG. 3. In addition, a partial sigF homolog is present in *M. leprae* (Acc. No. U00012); frameshift sequencing errors in the *M. leprae* sigF sequence may explain the incompleteness of this open-reading frame.

*M. tuberculosis* sigF has closest homology to *S. coelicolor* SigF, *B. subtilis* SigF, and *B. subtilis* SigB. The *S. coelicolor* SigF gene encodes a late-stage, sporulation-specific sigma factor. *S. coelicolor* SigF knockout mutants are unable to sporulate effectively producing deformed, thin-walled spores (17). *B. subtilis* SigF is essential for early spore gene expression. It is not transcribed until shortly after the start of sporulation (18), and its protein product is specifically activated within the developing forespore following septation (19). The *B. subtilis* SigB gene encodes a stress response sigma factor. While not an essential gene for growth or sporulation, SigB transcription is activated during stationary phase or under environmental stress, such as heat or alcohol shock (20, 21).

Lonetto et al. (11, 22) have divided the known sigma factors into a number of families based upon their primary structure homology patterns. The families include: primary sigma factors, a sporulation-specific group, a heat shock-related group, a flagellar-related group, and the newly recognized extracytoplasmic family. An important implication of these sequence homology clusters is that correlations between the primary structure and general function of bacterial sigma factors is preserved even across species barriers. The homology profile of *M. tuberculosis* sigF places it in the sporulation-specific family of such sigma factor classifications. This observation indicates that *M. tuberculosis* sigF has a functional role akin to those of the *S. coelicolor* and *B. subtilis* sigma factors to which it is similar.

EXAMPLE 4

Other mycobacteria which contain sigF-like genes

Southern blots were made from PvuII digested, mycobacterial genomic DNA obtained from clinical isolates. The blots were probed with a 285 base pair, *M. tuberculosis*-specific probe (nucleotides 1284 to 1568 of which SEQ ID NO:1) according to a previously published protocol (9). Hybridizations were performed overnight at 55° C. in buffer (5×SSC, 0.5% SDS, 5×Denhardt solution and 100 μ/ml sheared salmon sperm DNA) and were followed by five washes in 3×SSC at 45° C.

Southern blots of PvuII digested, mycobacterial, genomic DNA revealed sigF cross-hybridization in several slow-growing mycobacteria including *M. bovis* BCG (ATCC 35734) and clinical isolates of *M. avium, M. triviale*, and *M. gordonae*. The genomic DNA of rapid growing species like *M. smegmatis* and *M. abscessus* did not show hybridization by Southern blot analysis at intermediate stringency (50° C. hybridization and 40° C. washes in the above buffers).

*M. tuberculosis* sigF-like sequences were identified by Southern blot analysis in several slow growing mycobacterial species including *M. bovis* BCG and *M. avium. M. leprae* was known prior to this study to possess a sigF homolog on cosmid B1308 (Acc. No. U00012). Rapid growing species, such as *M. smegmatis* and *M. abscessus*, showed no sigF hybridization by Southern blot. The mycobacterial sigF gene may be associated with a developmental response unique to slow-growers. Alternatively, the absence of a sigF cross-hybridization in the rapidly growing species may simply be a function of increased evolutionary distance and decreased base pair homology.

EXAMPLE 5

Stress and stationary phase induction of sigF mRNA

Strains and plasmids: pYZ99 is pUC18 containing a 2.8 kb BamHI fragment of *M. tuberculosis* genomic DNA. pCK1845 is pCRII (Invitrogen, San Diego, Calif.) containing a 279 bp EcoRI/KpnI subclone of the *M. tuberculosis* sigF gene with an SP6 promoter site and a BamHI site at the 5' end of the sigF gene fragment and a T7 promoter site and an EcoRV site at the 3' end. Recombinant plasmids were constructed and transformed into *E. coli* DH5 by electroporation using standard protocols (8), and they were isolated and purified using the Qiagen system (Qiagen, Inc., Chatsworth, Calif.).

Mycobacterial cultures: Early exponential, late-exponential, and stationary phase Bacille Calmette-Guerin (*M. bovis* BCG, Pasteur strain, ATCC 35734) cultures were grown in standard Middlebrook 7H9 broth (Difco Laboratories, Detroit, Mich.) supplemented with ADC and Tween 80 (ADC-TW, ref. 11) at 37° C. with constant shaking. For cold shock, log phase cultures ($A_{600}$=0.78) were placed at 4° C. for 24 hours prior to harvesting. To test other stress conditions, log-phase cultures were centrifuged and resuspended in a stress broth at 37° C. with shaking for 24 hours. Stress broths consisted of Middlebrook 7H9-ADC-TW plus 10 mM $H_2O_2$ (oxidative stress) or 5% ethanol (alcohol stress). Nitrogen depleted medium was Middlebrook 7H9 containing only 10% of the standard amounts of glutamine and $NH_4Cl$. Microaerophilic cultures were prepared according to the settling method described by Wayne (10) for 7 days.

RNA extraction and quantification: Mycobacterial pellets were resuspended in extraction buffer (0.2M Tris, 0.5M NaCl, 0.01M EDTA, 1% SDS) plus an equal volume of phenol:chloroform:isoamyl alcohol (25:24:1). A 0.4 g aliquot of 300 μm prewashed glass beads (Sigma Chemical Company, St. Louis, Miss.) was added and the samples were vortexed for 2 minutes at high speed. After a brief centrifugation, the aqueous phase was removed, re-extracted with phenol:chloroform:isoamyl alcohol, and finally extracted with chloroform: isoamyl alcohol (24:1). The purified RNA was ethanol precipitated and quantified by $A_{260}$ measurement. Specific mRNA levels were determined by RNase protection assay (RPA, ref. 38) using a $^{32}P$-labeled, in vitro transcribed, sigF antisense RNA probe derived from BamHI-cut pCK1845 (Maxiscript system, Ambion, Austin, Tex). Control, nonlabeled sigF sense RNA was produced using the same DNA template cut with EcoRV, transcribed in the opposite direction. For each assay equal quantities of total mycobacterial RNA were tested.

Transcription of sigF was detected and monitored under different growth conditions of BCG, a slow-growing attenuated *M. bovis* strain which is a member of the *M. tuberculosis* complex, using an RNase protection assay (RPA, see FIG. 4). Our ability to protect a $^{32}P$-labeled sigF antisense RNA probe using total RNA isolated from *M. bovis* BCG using RPA analysis confirms that sigF is a transcribed gene in this close relative of *M. tuberculosis*. Replicate experiments showed that the RPA signal intensity results were reproducible to within 20% when performed with different batches of RNA on different days. The twin protected bands at 320 and 279 bases (FIG. 4) were observed consistently with the pCK1845-derived sigF antisense RNA probe. Secondary structure analysis of our probe reveals that about 40 bases of vector sequences at its 3' end are capable of forming a stem-loop which would protect a larger portion of the probe than the expected 279 bases. Both bands chase to 350 bases when a non-labeled, sense-strand RNA complementary over 350 bases is added. Thus, both bands result from protection of the probe by sigF mRNA.

In *M. bovis* BCG cultures, sigF transcription was strongly induced during stationary phase ($A_{600}$=2.7), nitrogen depletion, and cold shock. A weak RPA signal was present during late-exponential phase ($A_{600}$=1.5), oxidative stress (10 mM $H_2O_2$), microaerophilic culture conditions, and alcohol shock (5% ethanol). sigF mRNA was not detected during early exponential phase growth ($A_{600}$=0.67). The relative intensities of the RPA signals during different growth conditions is shown in Table 1.

RNase protection assays using an *M. tuberculosis* sigF-specific probe showed that the *M. tuberculosis* sigF open reading frame is a transcribed gene. Transcription was maximal during stationary phase, cold shock, and nitrogen depletion. Weaker RPA signals were present during other stress conditions, such as oxidative stress, alcohol shock, and microaerophilic stress. No evidence of transcription was seen during exponential-phase growth. RPA is highly sensitive and can detect mRNA at the femtogram level (23). These findings show that the *M. tuberculosis* sigF gene encodes a stationary phase/stress response sigma factor. This pattern of induction is similar to that of the *B. subtilis* sigB gene.

TABLE 1 sigF RPA signal relative to baseline for *M. bovis* BCG grown under different conditions.

| Growth Condition | RPA Signal Intensity* (relative to baseline) |
|---|---|
| Early Exponential Phase ($A_{600}$ = 0.67) | 1.0 |
| Late Exponential Phase ($A_{600}$ = 1.5) | 3.6 |
| Stationary Phase ($A_{600}$ = 2.7) | 9.8 |
| Oxidative Stress (10 mM $H_2O_2$) | 4.8 |
| Alcohol Shock (5% ethanol) | 2.8 |
| Cold Shock (4° C.) | 17.6 |
| Nitrogen Depletion | 8.8 |
| Microaerophilic Stress | 3.2 |

*Equal amounts of total bacterial RNA (0.85 μg) were used in each assay. Duplicate or quadruplicate aliquots of each stress culture were processed independently and average values are shown above. Quantitation was performed by digitally photographing the autoradiogram on an Ambis camera and then analyzing the bands on the NIH Imager program. Baseline was defined as the signal intensity at about 279–320 bases of early exponential phase samples, this was essentially the same as background.

EXAMPLE 6

*M. tuberculosis* sigF is antigenically more similar to *B. subtilis* SigB than to *B. subtilis* SigF Recombinant His-tagged sigF produced in *E. coli*: Using PCR amplification and primers with pre-designed compatible restriction sites, a pET15b-based expression vector called pLCD1 was constructed in which the T7 promoter was fused to the *M. tuberculosis* sigF gene. pLCD1 was constructed by ligating a 788 bp NdeI-SpeI digested PCR product amplified with primers HOS59 (5'-CATATGACGGCGCGCGCTGCCGGC-3', SEQ ID NO:12) and HOS61 (5'-ACTAGTTACTCCAACTGATCCCGTAG-3', SEQ ID NO:13) into pET15b digested with the same enzymes. *E. coli* BL21(DE3) transformed with pLCD1 were grown to mid-log phase ($OD_{600}$=0.6) in 50 ml of LB broth containing 50 μg/ml of ampicillin. Cultures were induced with 1 mM IPTG for 3 hours at 37° C., and this led to induction of high-level expression of sigF. The sigF protein partitioned with the insoluble fraction but could be readily resolubilized by denaturation with 6 M urea followed by dialysis. Nickel affinity chromatography as directed by the manufacturer (Novagen, Madison, Wis.) gave $His_6$-TCS-tagged sigF protein (TCS=thrombin cleavage site) which migrated at an estimated molecular mass of 32 kDa and was >90% pure. The deduced molecular mass of untagged sigF is 29,985 daltons. This process yields about 4.5 mg or purified protein per 250 ml of culture.

Antibodies were produced in New Zealand white rabbits immunized intradermally (primary inoculation) and subcutaneously (three boosts) with 375 mg each time of purified recombinant M. tuberculosis sigF (HRP Inc., Denver, Pa.).

In view of the similarities between the genomic organization of the M. tuberculosis sigF locus and that for B. subtilis sigF and sigB, it was determined whether M. tuberculosis sigF was more related to B. subtilis sigF (sporulation) or B. subtilis sigB (stress response). Western blotting was performed to ascertain the degree of antigenic cross-reactivity between the three sigma factors using antibodies which were raised against purified M. tuberculosis sigF as well as similar antibodies raised against B. subtilis SigF.

Purified B. subtilis SigB, B. subtilis SigF, and rabbit antisera against B. subtilis SigF were kindly provided by L. Duncan and R. Losick. Proteins (10 mg/well) were separated by SDS-PAGE (12.5%) and then transferred by capillary action to Protran membranes (Schleicher and Schuell, Keene, N.H.). Membranes were blocked with BLOTTO/Tween (5% dry non-fat milk, 0.2% Tween 20 and 0.02% sodium azide in phosphate buffered saline) and then incubated with unpurified rabbit sera. Antibody binding was detected using alkaline phosphatase conjugated goat anti-rabbit antibodies (Sigma Immunochemicals, St. Louis, Mo.) and developed with bromochloroindolyl phosphate/nitro blue tetrazolium (BCIP/NBT).

Antibodies against M. tuberculosis sigF showed greater cross-reactivity to B. subtilis SigB than to B. subtilis SigF, suggesting that M. tuberculosis sigF is antigenically more similar to B. subtilis SigB than to B. subtilis SigF. Antibodies against B. subtilis SigF cross-reacted essentially equally with M. tuberculosis sigF and B. subtilis SigB.

With purified recombinant M. tuberculosis sigF and orfX, and antibodies for each available, in vitro interaction between the two proteins was evaluated with the amino-specific crosslinker ethylene bis(succinimidylsuccinate) (EGS as used in ref. 47) and Western blotting with anti-orfX antiserum. M. tuberculosis orfX readily dimerizes in the presence of EGS even when no M. tuberculosis sigF is added. When both M. tuberculosis sigF and EGS are included, high molecular weight (>50 kDa) complexes are obtained. M. tuberculosis sigF and EGS alone are not detected by the anti-orfX antibody. Such patterns of crosslinking have also been demonstrated with B. subtilis SigF and SpoIIAB by Richard Losick.

EXAMPLE 7

Effect of expressing the M. tuberculosis sigF locus

Recombinant plasmids: pYZ103 was derived by cloning a 1.6 kb KpnI fragment from pYZ99 into the unique KpnI site of p16R1 (39). pCK99 and pCK99R were derived by subcloning a 2.8 kb BamHI fragment from pYZ99 into the unique BamHI site of pNBV1 (40); in pCK99 the XbaI site of the vector is 5' of the sigF gene while the insert is in the opposite orientation with respect to the vector in pCK99R. pCK99F1 was made by deleting a 2.0 kb HindIII fragment from pCK99. Similarly, pCK99R16 and pCK99R11 were formed by deleting 0.8 kb BstXI and 0.8 kb HindIII fragments from pCK99 respectively. pCK1 was constructed by cloning a 1.5 kb EcoRI-HindIII fragment from pCK99 into EcoRI-HindIII digested pMV261 (41). Later, the frame-shifted fusion construct pCK1M was made by filling in the EcoRI site of pCK1 using E. coli DNA polymerase large fragment (Klenow) and religating the blunted ends. The restriction map of the M. tuberculosis sigF locus is illustrated in FIG. 1.

Mycobacterial transformation: Electrocompetent mycobacteria were produced by growing cultures in standard Middlebrook 7H9 broth (Difco Laboratories, Detroit, Mich.) supplemented with albumin-dextrose complex (ADC) and Tween-80 (42) until mid-log phase ($OD_{600}$=0.6). Bacterial cells were transformed with 0.2 μg of purified plasmid using a Bio-Rad E.coli Pulser apparatus (Bio-Rad Laboratories, Hercules, Calif.) set for 2.5 kV and 200Ω and 0.1 cm gap cells. After 3 or 24 hours of recovery in Middlebrook 7H9 liquid media supplemented with ADC and Tween-80 for M. smegmatis or M. bovis BCG respectively, transformed cells were selected on Middlebrook 7H10 media supplemented with ADC, cycloheximide, and either 50 mg/ml hygromycin or 10 mg/ml kanamycin. To monitor growth rate, the greatest diameter of 25 randomly selected colonies were measured on day 15 after plating using a dissecting microscope with a gridded eyepiece.

Overexpression of segments of the M. tuberculosis sigF locus in M. bovis BCG. Genes may be overexpressed in mycobacteria by introducing them on multicopy plasmids or by fusing them to strong, constitutive mycobacterial promoters. To determine whether phenotypic differences might be detectable upon overexpression of orfY alone or orfY+orfX without sigF, we deleted portions of the 2.8 kb sigF locus contained within pCK99. The truncated segments were derivatives of multicopy plasmid vectors, p16R1 (39) or pNBV1 (40), which confer hygromycin resistance. Each construct except pCK99R11 contains the 238 bp 5' untranslated region (5'UTR) upstream of orfY in which promoters similar to those recognized by *B. subtilis* SigF and *S. coelicolor* WhiG are found. After introduction of the constructs into *M. bovis* BCG by electroporation and selection in the presence of hygromycin, the growth rate (colony size after 15 days) and colony morphology of each of the recombinant strains was evaluated.

By introducing these constructs as multicopy plasmids, they would be overexpressed due to the increase in gene number. With the *B. subtilis* sigB and sigF operons, the anti-anti-sigma, anti-sigma, and sigma genes are transcribed as an operon ensuring balanced expression of the proteins. These experiments were designed to determine if the introduction of additional copies of orfX and/or orfY, leading to an imbalance in the copy numbers of these potential regulatory proteins, might produce gross phenotypic changes. As may be seen in Table 2, only minor differences were detected in growth rates following the introduction of the truncated forms, and no changes in colony morphology were seen.

TABLE 2

Growth rate and colony morphology of *M. bovis* BCG transformants harboring varying segments of the sigF locus

| | Relevant Contents | Average Colony Diameter on Day 15 (mm)* | Colony Morphology |
|---|---|---|---|
| pCK99 | 5'UTR, orfY, orfX, sigF | 0.88 ± 0.13 | wild type |
| pYZ103 | 5'UTR, orfY, orfX | 1.02 ± 0.12 | wild type |
| pCK99F1 | 5'UTR, orfY | 0.86 ± 0.13 | wild type |
| pCK99R16 | 5'UTR, orfY, orfX, sigF | 0.90 ± 0.13 | wild type |
| pCK99R11 | sigF | 0.92 ± 0.13 | wild type |
| pNBV1 | empty vector | 0.91 ± 0.12 | wild type |

*Mean greatest diameter of 25 randomly selected colonies evaluated ± one standard deviation.

Overexpression of *M. tuberculosis* sigF in *M. bovis* BCG by fusion to the hsp60 promoter. Since merely increasing the copy number of the sigF locus and introducing various truncated forms of the locus did not alter the agar growth rate or the colony morphology of *M. bovis* BCG, the sigF gene was fused to a strong constitutive promoter and evaluated the effect of inappropriate expression of the gene. A unique EcoRI restriction site situated close to the beginning of the sigF translation start site was used to fuse the sigF gene to the hsp60 promoter present in pMV261 (41). The resulting in-frame fusion (carried in plasmid pCK1 ) was predicted to encode a 237 aa protein consisting of Hsp60 residues 1 to 10 and sigF residues 35 to 261. As a control, a 4 bp frameshift was introduced at the junction between the hsp60 and sigF genes by filling in the cohesive end produced by EcoRI. Because of the frameshift, this construct called pCK1M would be expected to produce a short nonsense protein instead of the $sigF_{35-261}$ protein. The derivation of pCK1 and pCK1M is detailed above.

Transformation of *M. bovis* BCG and selection on 7H10 agar with kanamycin yielded numerous colonies when pMV261 (empty vector) was used. However, only a few transformants (probably spontaneous kanamycin-resistant mutants) survived when pCK1 or no DNA was used for electroporation. The introduction of a frameshift mutation between the hsp60 promoter and the sigF gene with pCK1M restored transformability to the plasmid (175–275 colony forming units per 0.1 $\mu$g). pCK1M does not transform *M. bovis* BCG as efficiently as the empty vector pMV261. This may represent a partial toxicity associated with high level expression of the hsp60-driven nonsense fusion protein. These experiments indicate that growth of *M. bovis* BCG is incompatible with constitutive overexpression of sigF from a strong promoter.

The three plasmids, pMV261, pCK1, and pCK1M have also been used to transform the rapid-grower, *M. smegmatis*. Example 4 indicated that *M. smegmatis* does not have a sigF homolog as assessed by Southern blotting and, moreover, PCR with degenerate primers synthesized according to the sigF sequence does not detect a sigF homolog in *M. smegmatis*. All three plasmids including pCK1 were found to transform *M. smegmatis* cells to kanamycin-resistance with high efficiency, and no colony-morphology changes were detected in the *M. smegmatis*/pCK1 transformants. These results suggest that growth incompatibility associated with high level, constitutive sigF expression is specific to *M. bovis* BCG. These observations provide support that expression of sigF-dependent genes prevents growth because such genes are involved in a program of growth arrest in response to starvation or stress.

During exponential growth in rich medium the sigF gene was transcriptionally silent in *M. bovis* BCG, and constitutive overexpression of *M. tuberculosis* sigF is incompatible with growth in *M. bovis* BCG (a slow-grower known to have sigF) but without effect in *M. smegmatis* (a rapid-grower which does not have a sigF homolog). While we have not established the precise mechanism of toxicity of sigF overexpression, one possibility is that sigF-dependent genes participate in growth arrest and entry into stationary phase and thus block growth when inappropriately expressed. An alternative explanation is that excess sigF protein sequesters core RNA polymerase blocking its association with the principal sigma which is needed for transcription of genes for vegetative growth. The ability of *M. smegmatis* to tolerate sigF overexpression argues against this latter explanation since there are unlikely to be major differences between the core polymerases of slow and rapid growers (43).

By comparison, overexpression of the *B. subtilis* sigF gene from the inducible promoter $P_{spac}$ in *B. subtilis* leads to the production of small colonies which lyse after one to two days when constitutively induced in the presence of IPTG (26). Moreover, constitutive production of *B. subtilis* sigF in *E. coli* was reported to be incompatible with growth even when expression was presumed to be relatively weak and the estimated concentration of sigF molecules per cell was well below that for native *E. coli* RpoD, the principal sigma. Significantly, neither *B. subtilis* sigF nor sigB is completely lethal when overexpressed in *B. subtilis* as appears to be the case with *M. tuberculosis* sigF overexpression in *M. bovis* BCG.

EXAMPLE 8

In vivo expression of *M. tuberculosis* sigF

An in-frame translational lacZ-kan fusion within the *M. tuberculosis* sigF gene was constructed from the multi-copy vector pNBV1 (40). The unique EcoRI site at nucleotide 1284 of SEQ ID NO:1 was digested with EcoRI, the EcoRI-generated overhangs were filled with Klenow fragment, and a BamHI site was created by ligation of BamHI linkers at the blunt ends. As a result, the EcoRI site was recreated and a unique BamHI site was inserted; this was verified by DNA sequencing (5'-TCA CCG GAATTC GGATCC GTC GAC CTG-3', SEQ ID NO:14). The 4.0 kb BamHI cassette carrying lacZ-kan from pLZK82 (48) was inserted into the synthetic BamHI site. An error in the reported sequence of pLZK82 was corrected by patching oligonucleotides at the EcoRI site: top strand is 5'-AATTGTTTAAACGCTTAATT-3' (SEQ ID NO:15) and bottom strand is 5'-AATTAATTAAGCGTTTAAAC-3' (SEQ ID NO:16). The 6.8 kb gene fusion was excised by digestion with PacI and SapI, and the blunted fragment was inserted into the EcoRV site of pNBV1. This construct (pCK3127) contains both the *M. tuberculosis* usfY and usfX genes as well as about 250 bp of 5'UTR upstream of *M. tuberculosis* usfY. Strains harboring this construct may be considered *M. tuberculosis* sigF expression indicators.

A mycobacterial integrative version of this same construct has also been made (pCK3215) with the integrative vector pMH94 (49), along with the corresponding strain.

In vitro conditions would be expected to modulate *M. tuberculosis* sigF expression, and in support of this expectation, *M. bovis* BCG transformants harboring either the multi-copy pCK3127 or the integrative pCK3215 construct give interesting target colony patterns with central accumulation of hydrolyzed XGal; an out-of-frame control plasmid was not stained. This pattern indicates that only the bacteria in the center of the colony where nutrients are limited expressed sigF. *M. smegmatis* transformants harboring the same constructs remain white (not having a sigF homolog, *M. smegmatis* would presumably not have a system of regulating sigF) while an hsp60::lacZ gene fusion in *M. bovis* BCG gave uniformly blue colonies. Thus, *M. tuberculosis* sigF transcription can be induced by stress and stationary phase.

The sigF::lacZ reporter gene in *M. bovis* BCG expresses sigF following entry into murine macrophages. At t=0, *M. bovis* BCG harboring pCK3127 (i.e., the multicopy plasmid sigF::lacZ gene fusion) was used to infect murine J774 macrophage cells at multiplicity of infections of 5–10:1 in antibiotic-free MEM supplemented with 10% fetal bovine serum, 5% NCTC109, 1% gelatin, and 1% non-essential amino acids. After co-incubation for 5 hours (t=5 hr) the macrophages were washed and incubated in fresh MEM with supplements until t=24 or 48 hr. To measure mycobacterial sigF gene expression during infection, the macrophages were washed with PBS and then harvested with a rubber policeman. Saponin (0.1%) was added to lyse the macrophages, and the liberated *M. bovis* BCG were recovered by 3 cycles of centrifugation and washing in PBS on ice. Isolated *M. bovis* BCG were lysed by 10 min of vortexing in Miller buffer Z in the presence of 300 μm glass beads. This lysate of purified intracellular *M. bovis* BCG was used for measurements of β-galactosidase activity by the method of Miller or by the methyl umbelliferyl D-galactoside (MUG) method; total viable bacteria were estimated by the $^3$H-uracil uptake assay. SigF-specific activity was expressed as units of β-galactosidase per cpm of $^3$H-uracil.

In vivo expression of *M. tuberculosis* sigF was also shown by infecting J774 macrophages with *M. bovis* BCG harboring the multicopy sigF::lacZ/kan fusion (pCK3127) and evaluating the activity of β-galactosidase in *M. bovis* BCG harvested from the macrophages at various times. The β-galactosidase activity was indexed to a measurement of the number of metabolically active *M. bovis* BCG measured by $^3$H-uracil uptake. sigF reporter gene specific activity measured in this manner increased steadily over the 72 hour observation period. This shows that sigF expression is associated with the intracellular growth of *M. bovis* BCG. Further, it suggests that sigF may control an intracellular survival regulon.

EXAMPLE 9
sigF-dependent transcription of a promoter in the *M. tuberculosis* sigF locus In vitro transcription was used to identify a $P_{csf}$ (promoter controlled by *M. tuberculosis* sigF). The in vitro transcription (IVT) assay was developed by overexpressing and purifying recombinant His$_6$-sigF in *E. coli*, and reconstituting activity with either *Streptomyces coelicolor* core RNA polymerase provided by Mary Brawner (50) or *E. coli* core RNA polymerase (Epicenter, Madison, Wis.). Prior to addition of DNA template, 2 units of core RNA polymerase was incubated with 2 μg sigma factor for 30 min at 37° C.; the reaction buffer was 40 mM Tris-HCl (pH 8.0), 10 mM MgCl$_2$, 0.1 mM EDTA, 0.1 mM dithiothreitol, 0.25 mg/ml bovine serum albumin and 10% glycerol. Addition of 2 μg DNA template and incubation for 15 min at 37° C. allowed protein-DNA interaction; transcription was initiated by adding ribonucleotides (0.15 mM each of ATP, UTP and GTP, and 0.4 μM [α-$^{32}$P]CTP). After 3 min, cold CTP to a final concentration of 0.15 mM and heparin were added and incubation continued for another 15 min. The in vitro transcription reaction was terminated by addition of formamide loading dye and boiling for 10 min, prior to loading the gel.

As a target promoter, a 265 bp PCR product consisting of the 5'UTR upstream of *M. tuberculosis* usfY and a portion of the *M. tuberculosis* usfY coding sequence was used (nucleotides 170 to 434 of SEQ ID NO:1). The −35 region consists of nucleotides 190 to 194 of SEQ ID NO:1, the −10 region consists of nucleotides 210 to 218 of SEQ ID NO:1, and the Shine-Dalgarno sequence consists of nucleotides 229 to 234 of SEQ ID NO:1. The *M. tuberculosis* sigF-dependent IVT assay produces a 225 base transcript, which is consistent with transcription from the 12/14 base *B. subtilis* SigF-like promoter upstream of usfY originating between the −10 region and the Shine-Dalgarno sequence. Thus, the *M. tuberculosis* sigF locus appears to be autoregulated.

EXAMPLE 10
Indicator strains for sigF expression and sigF activity

Two different indicator strains bearing either pCK3127 or pCK3215 are provided, and similar strains can be constructed with *M. tuberculosis*, to screen for agents that affect sigF expression, or sigF activity. The effect may be a quantitative increase or decrease, or a qualitative difference (e.g., faster or slower kinetics, accelerated or delayed lags), or a combination of qualitative and quantitative.

The indicator strains described above may use an indicator gene which makes a product that is directly detectable, or both the product of the indicator gene and a substrate may be required to make a detectable indicator product. Products that are directly detectable include, for example, nucleic acids (e.g., amplification, hybridization) and proteins (e.g., ligand-receptor binding, aggregation, crystallization). Indicator genes include lacZ, xylE, luxAB, gfp, and melC. Radioactive decay, photon production, light scattering, and UV-VIS light absorbance may be detected.

Agents that affect sigF expression may be screened using the indicator strain described above. β-Galactosidase substrates ONPG (yellow) or XGal (blue) may be used. Agents may be evaluated in two ways: cells growing exponentially in rich medium (sigF normally off) for premature induction of sigF expression, and cells starved for nitrogen (sigF normally on) for inability to induce sigF expression. Known antimycobacterial drugs may be assayed to validate the method, bacteriocidal drugs (e.g., isoniazid, rifampin, pyrazinamide, streptomycin) and bacteriostatic drugs (e.g., ethambutol, para-amino salicylate, thiacetazone). Culture conditions may also be evaluated for their potential to induce a stress response by adding chemicals (e.g., hydrogen peroxide, sodium nitroprusside which liberates nitric oxide, EDDA which chelates iron and produces iron starvation) to the medium.

*M. tuberculosis* can survive for relatively long periods in expectorated sputum. Survival outside the human host requires adaptation to oxidative stress, low nutrient levels, and low temperature. The biochemical and genetic alterations permitting the organism to survive under these conditions are unknown. All of these conditions, in particular cold shock, induce *M. tuberculosis* sigF transcription. It is possible that sigF is important for survival outside of the host. *M. tuberculosis* sigF is involved in the adaptation of the organism during latent infection. The observation that *M. tuberculosis* has a sigma factor closely related to sporulation sigmas from *S. coelicolor* and *B. subtilis* is intriguing since tubercle bacilli are classically described as non-sporulating bacilli. Both the *B. subtilis* SigB and SigF genes are transcribed as parts of polycistronic messages containing post-translational regulatory genes (24–28). The sigB operon encodes three other genes (rsbV, rsbW, and rsbX) which control SigB activation. The *B. subtilis* SigF operon encodes two other genes encoding an anti-sigma factor (SpoIIAB) and an anti-anti-sigma factor (SpoIIAA). The *S. coelicolor* SigF gene appears to be monocistronic (17).

An important question in characterizing *M. tuberculosis* sigF is to determine whether it is functionally related to *B. subtilis* SigB, a regulator of stress response, or *B. subtilis* SigF, a developmental regulator of sporulation. Our findings lead us to conclude that *M. tuberculosis* sigF is more closely related to *B. subtilis* SigB than to *B. subtilis* SigF. The protein sequence of *M. tuberculosis* sigF revealed 30% amino acid identity to *B. subtilis* SigB compared to 26% to *B. subtilis* SigF. Western blot data confirm this relationship: *B. subtilis* SigB cross-reacted more strongly than *B. subtilis* SigF with polyclonal antibodies directed against *M. tuberculosis* sigF. On the other hand, the genomic organization of the *M. leprae* and *M. tuberculosis* sigF loci resembles that of the *B. subtilis* sigF operon since the mycobacterial gene clusters lack homologs of the regulatory genes, rsbX and rsbRSTU, which surround the *B. subtilis* sigB locus.

As a *B. subtilis* SigB-like stress response sigma factor, *M tuberculosis* sigF might down-regulate genes essential for rapid growth and/or upregulate genes which defend against harsh environmental conditions. Alternatively, *M. tuberculosis* sigF may be involved in a change of cell type as is seen with *B. subtilis* SigF and *S. coelicolor* SigF. Tubercle bacilli can remain latent within the human host for decades. The nature of the organisms during latency is poorly understood, although Wayne and colleagues have reported that gradual oxygen withdrawal from *M. tuberculosis* cultures leads to the development of non-replicating persistent states in a liquid culture model.

If the *M. tuberculosis* sigF regulon contains genes which shift the cell into non-replicating persistence, then characterization of sigF-dependent genes might offer important insights into the important health problem of latent tuberculosis. Such molecular genetic studies using the *M. tuberculosis* sigF gene may help address the question of whether tubercle bacilli enter a spore-like state during persistent infection.

The disclosures of all journal articles, texts, and patents cited in this specification are incorporated herein by reference in their entirety. In particular, the priority documents U.S. Pat. application Ser. Nos. 08/622,352 and 08/622,353 are incorporated by reference in their entirety.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

REFERENCES

1. Smith, P. G., and Moss, A. R. 1994. in *Tuberculosis: Pathogenesis, Protection, and Control*, Bloom, B. R. (ed.), (ASM Press, Washington, D.C.), pp. 47–59.
2. Bloom, B. R., and Murray, C. J. L. 1992. *Science* 257, 1055–1064.
3. Gedde-Dahl, T. 1952. *Am. J. Hyg.* 56, 139–214.
4. Sudre, P., ten Dam, G., and Kochi, A. 1992. *Bull. WHO* 70, 149–159.
5. Wayne, L. G. 1994. *Eur. J. Clin. Microbiol. Infect.* Dis. 13, 908–914.
6. Khomenko, A. G. 1980. *Probl. Tuberk* 2, 18–23.
7. Werner, G. H. 1954. *Am. Rev. Tuberc.* 69, 473–474.
8. Ausubel, F. M., Brent, R., Kingston, R. E., Moore, D. D., Seidman, J. G., Smith, J. A., and Struhl, K. 1994. *Current Protocols in Molecular Biology* (John Wiley and Sons, Inc.), pp. 1.8.4–1.8.8.
9. Sambrook, J., Fritsch, E. F., and Maniatis, T. 1989. *Molecular Cloning: A Laboratory Manual* (CSHL Press, Plainview, N.Y.), pp. 9.31–9.57.
10. Wayne, L. G. 1976. *Am. Rev. Resp. Dis.* 114, 807–811.
11. Lonetto, M., Gribskov, M., and Gross, C. A. 1992. *J. Bacteriol.* 1764, 3843–3849.
12. Gross, C. A., Lonetto, M., and Losick, R. 1992. in *Transcriptional Regulation*, McKnight, S. L., and Yamamoto K. R. (eds.), (CSHL Press, Plainview, N.Y.), Vol. 1, pp. 129–176.
13. Predich, M., Doukhan, L., Nair, G., and Smith, I. 1995. *Mol. Microbiol.* 15, 355–366.
14. Kempsell, K. E., Ji, Y. E., Estrada, I. C., Colston, M. J., and Cox, R. A. 1992. *J. Gen. Microbiol.* 138, 1717–1727.
15. Honore, N., Bergh, S., Chanteau, S., Doucet-Populaire, F., Eiglmeier, K., Garnier, T., Georges, G., Launois, P., Limpaiboon, T., Newton, S., Niang, K., del Portillo, P., Ramesh, G. R., Reddi, P., Ridel, P. R., Sittisombut, N., Wu-Hunter, S., and Cole, S. T. 1993. *Mol. Microbiol.* 7, 207–214.
16. Tanaka, K., Shiina, T., and Takahashi, H. 1988. *Science* 242, 1040–1042.
17. Potuckova, L., Kelemen, G. H., Findlay, K. C., Lonetto, M. A., Buttner, M. J., and Kormanec, J. 1995. *Mol. Microbiol.* 17, 37–48.
18. Gholamhoseinian, A., and Piggot, P. J. 1989. *J. Bacteriol.* 171, 5747–5749.
19. Margolis, P., Driks, A., and Losick, R. 1991. *Science* 254, 562–565.
20. Benson, A. K., and Haldenwang, W. G. 1993. *J. Bacteriol.* 175, 2347–2356.
21. Boylan, S. A., Redfield, A. R., Brody, M. S., and Price, C. W. 1993. *J. Bacteriol.* 175, 7931–7937.
22. Lonetto, M., Brown, K. L., Rudd, K., and Buttner, M. J. 1994. *Proc. Natl. Acad. Sci. USA* 91, 7573–7577.
23. Haines, D. S., and Gillespie, D. H. 1992. *Biotechniques* 12, 736–740.
24. Kalman S., Duncan, M., Thomas, S., and Price, C. W. 1990. *J. Bacteriol.* 172, 5575–5585.
25. Benson, A. K., and Haldenwang, W. G. 1993. *Proc. Natl. Acad. Sci. USA* 90, 2330–2334.
26. Schmidt, R., Margolis, P., Duncan, L., Coppolecchia, R., Moran Jr., C. P., and Losick, R. 1990. *Proc. Natl. Acad. Sci. USA* 87, 9221–9225.
27. Min, K. T., Hilditch, C. M., Dieterich, B., Errington, J., and Yudkin, M. D. 1993. *Cell* 74, 735–742.
28. Alper, S., Duncan, L., and Losick, R. 1994. *Cell* 77, 195–205.
29. Schuler, G. D., Altschul, S. F., and Lipman, D. J. 1991. *Proteins Struct. Funct. Genet.* 9, 180–190.
30. Stanford, J. L. 1987. *Tubercle* 68, 241–242.
31. Csillag, A. 1964. *J. Gen. Microbiol.* 34, 341.
32. Khomenko, A. G. 1987. *Tubercle* 68, 243–253.
33. Barksdale, L., Convit, J., Kim, K.-S., and de Pinardi, M. E. 1973. *Biochem. Biophys. Res. Comm.* 54, 290.
34. Chatterjee, B. R. 1976. *Leprosy in India* 48, 398.
35. Roek, G. A. W., and Stanford, J. L. 1992. *Immunol. Today* 13, 160–164.
36. Fidler, H. M., Rook, G. A., Johnson, N. M., and McFadden, J. 1993. *Brit. Med. J.* 306, 546–549.
37. Haldenwang, W. G. 1995. *Microbiol. Rev.* 59, 1–30.
38. Firestein, G. S., Gardner, S. M., and Roeder, W. D. 1987. *Anal. Biochem.* 167, 381–386.
39. Garbe, T. R., Barathi, J., Barnini, S., Zhang, Y., Abou-Zeid, C., Tang, D., Mukherjee, R., and Young, D. B. 1994. *Microbiology* 140, 133–138.

40. Howard, N. S., Gomez, G. E., Ko, C., and Bishai, W. R. 1995. *Gene* 166, 181–182.
41. Stover, C. K., de la Cruz, V. F., Fuerst, T. R., Burlein, J. E., Benson, L. A., Bennett, L. T., Bansal, G. P., Young, J. F., Lee, M. H., Hatfull, G. F., Snapper, S. B., Barletta, R. G., Jacobs Jr., W. R., and Bloom, B. R. 1991. *Nature* 351, 456–460.
42. Jacobs, W. R., Kalpana, G. V., Cirillo, J. D., Pascopella, L., Snapper, S. B., Udani, R. A., Jones, W., Barletta, R. G., and Bloom, B. R. 1991. *Meth. Enzymol.* 204, 537–555.
43. Bashyam, M. D., Kaushal, D., Dasgupta, S. K., and Tyagi, A. K. 1996. *J. Bacteriol.* 178, 4847–4853.
44. Duncan, L., and Losick, R. 1993. *Proc. Natl. Acad. Sci. USA* 90, 2325–2329.
45. Levin, M. E., and Hatfull, G. F. 1993. *Mol. Microbiol.* 8, 277–285.
46. Moran, C. P. 1990. in *Molecular Biological Methods for Bacillus*, Harwood, C. R., and Cutting, S. M. (eds.), (Wiley, Chichester, England), pp. 267–293.
47. Browning, J., and Ribolini, A. 1989. *J. Immunol.* 143, 1859–1867.
48. Barcak, G. J., Chandler, M. S., Redfield, R. J., and Romb, J.-F. 1991. *Meth. Enzymol.* 204, 321–342.
49. Lee, H. M., Pascopella, L., Jacobs, W. R., and Hatfull, G. F. 1991. *Proc. Natl. Acad. Sci. USA.* 88, 3111–3115.
50. Babcock, M. J., Buttner, M. J., and Brawner, M. E. 1995. *Abstracts of the Am. Soc. Microbiol. 95th General Meeting Abstract* H-203, pg. 527.

We claim:

1. A method of identifying compounds which regulate the binding of *M. tuberculosis* sigF to *M. tuberculosis* orfX, comprising the steps of:

incubating *M. tuberculosis* sigF immobilized on a solid support with a test compound and *M. tuberculosis* orfX; and determining the amount of the *M. tuberculosis* orfX which is bound to the *M. tuberculosis* sigF, a desirable test compound being one which increases or decreases binding of the *M. tuberculosis* orfX to *M. tuberculosis* sigF.

2. The method of claim 1 wherein *M. tuberculosis* orfY is also incubated with the sigF, the test compound, and the orfX.

3. A method of identifying compounds which regulate the binding of *M. tuberculosis* sigF to *M. tuberculosis* orfX, comprising the steps of:

incubating *M. tuberculosis* orfX immobilized on a solid support with a test compound and *M. tuberculosis* sigF; and determining the amount of the *M. tuberculosis* sigF which is bound to the *M. tuberculosis* orfX, a desirable test compound being one which increases or decreases binding of the *M. tuberculosis* sigF to *M. tuberculosis* orfX.

4. The method of claim 3 wherein *M. tuberculosis* orfY is also incubated with the sigF, the test compound, and the orfX.

5. The method of claim 1 wherein sigF is a polypeptide represented by SEQ ID NO:2 and orfX is a polypeptide represented by SEQ ID NO:3.

6. The method of claim 2 wherein sigF is a polypeptide represented by SEQ ID NO:2, orfX is a polypeptide represented by SEQ ID NO:3 and orfY is a polypeptide represented by SEQ ID NO:4.

7. The method of claim 3 wherein sigF is a polypeptide represented by SEQ ID NO:2 and orfX is a polypeptide represented by SEQ ID NO:3.

8. The method of claim 4 wherein sigF is a polypeptide represented by SEQ ID NO:2, orfX is a polypeptide represented by SEQ ID NO:3 and orfY is a polypeptide represented by SEQ ID NO:4.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 2000 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Mycobacterium tuberculosis (xi) SEQUENCE DESCRIPTION: SEQ ID NO:1:

```
TGGTGGGGAT GGCACGGCGC CGGCTGGTTT TTGTTGACGC TGATGGTGCT          50

GACGCTCTGC ATAGGCGTCC CACCGATCGC CGGCCCGGTC ATGGCGCCGT         100

GAGCCGTCGG CCAGGTCGGC CGCGGTCAAC AAATAAATGG GTCAGATCCC         150

TCCACAACCC GTTCGACGAG TTCTACCGTT GATGGTAGTG CCTGGTAATG         200

GGCAGAAATG GCGGAATAGG ACGGAAACGG AGGAGGCCAT GGGCGACACC         250

TATCGTGACC CCGTCGACCA CTTGCGGACG ACGCGGCCGC TTGCCGGCGA         300

GTCGCTGATC GACGTGGTGC ATTGGCCTGG GTATCTGTTG ATTGTGGCCG         350

GTGTCGTCGG CGGCGTCGGA GCTCTTGCGG CTTTCGGCAC CGGACATCAC         400

GCCGAGGGCA TGACCTTTGG TGTGGTGGCG ATTGTCGTCA CAGTGGTTGG         450

TTTGGCGTGG CTAGCGTTCG AGCATCGGCG GATACGCAAG ATTGCCGATC         500

GCTGGTATAC CGAACATCCC GAAGTCCGGC GGCAGCGGCT GGCCGGCTAG         550

ACATCCTAGT GCGGCTGGAA ATCCCGGCAT CGCGGGTTT CACCGGCAGC          600

TGCGAATGGG TATCACGGGT ACACCATGAT GAATCCCGAC CATGTTGCGT         650

TAGATCCCCA CTACCAGCAG GTCCGACCAT GACCGACCAG CTCGAAGACC         700

AGACCCAAGG CGGGAGTACT GTCGATCGAA GCTTGCCGGG AGGGTGCATG         750

GCCGACTCGG ATTTACCCAC CAAGGGGCGC CAACGCGGTG TCCGCGCCGT         800

CGAGCTGAAC GTTGCTGCCC GCCTGGAGAA CCTGGCGCTG CTGCGCACCC         850

TGGTCGGCGC CATCGGCACC TTCGAGGACC TGGATTTCGA CGCCGTGGCC         900
```

```
GACCTGAGGT TGGCGGTGGA CGAGGTGTGC ACCCGGTTGA TTCGCTCGGC         950

CTTGCCGGAT GCCACCCTGC GCCTGGTGGT CGATCCNCGA AAAGACGAAG        1000

TTGTGGTGGA GGCTTCTGCT GCCTGCGACA CCCACGACGT GGTGGCACCG        1050

GGCAGCTTTA GCTGGCATGT CCTGACCGCG CTGGCCGACG ACGTCCAGAC        1100

CTTCCACGAC GGTCGCCAGC CCGATGTAGC CGGCAGTGTC TTCGGCATCA        1150

CGTTGACCGC CCGACGGGCG GCATCCAGCA GGTGACGGCG CGCGCTGCCG        1200

GCGGTTCTGC ATCGCGAGCT AACGAATACG CCGACGTTCC GGAGATGTTT        1250

CGCGAGCTGG TTGGTTTGCC TGCCGGCTCA CCGGAATTCC AGCGGCACCG        1300

GGACAAGATC GTTCAGCGGT GCTTGCCGCT GGCCGATCAC ATCGCGCGGC        1350

GGTTCGAGGG TCGCGGCGAA CCGCGTGACG ACCTTATTCA GGTCGCGCGG        1400

GTCGGGCTGG TCAACGCCGC GGTTCGCTTC GACGTGAAGA CCGGGTCGGA        1450

CTTCGTCTCC TTCGCGGTTC CTACCATCAT GGGCGAGGTC CGACGACACT        1500

TCCGCGACAA CAGCTGGTCG GTCAAGGTTC CCCGGCGTCT CAAGGAACTG        1550

CATCTGCGGC TAGGTACCGC CACCGCCGAT TTGTCGCAGC GGCTCGGGCG        1600

GGCGCCGTCG GCATCGGAGC TCGCCGCGGA GCTCGGGATG GACCGCGCTG        1650

AGGTTATCGA AGGTTTGCTG GCGGGTAGTT CCTACCACAC CTTGTCCATC        1700

GACAGCGGTG GCGGCAGCGA CGACGATGCC CGCGCAATCA CAGACACCCT        1750

GGGCGACGTG GATGCGGGTC TTGACCAGAT CGAGAATCGG GAGGTGCTTC        1800

GTCCGTTGCT CGAGGCGTTG SCCGAGCGGG AACGAACGGT CTTGGTGCTC        1850

AGGTTCTTCG ACTCGATGAC CCAAACGCAG ATCGCCGAGC GCGTCGGTAT        1900

CTCACAGATG CACGTGTCGC GGGTGCTGGC CAAGTCATTG GCACGGCTAC        1950

GGGATCAGTT GGAGTAGCCG CCGGGCTTAC TTGGATCTCG GCGRAGCACC        2000
```

(2) INFORMATION FOR SEQ ID NO:2:

(i) SEQUENCE CHARACTERISTICS:
        (A) LENGTH: 261 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Mycobacterium tuberculosis (xi) SEQUENCE DESCRIPTION: SEQ ID NO:2:

```
Met Thr Ala Arg Ala Ala Gly Gly Ser Ala Ser Arg Ala Asn Glu Tyr
1               5                   10                  15

Ala Asp Val Pro Glu Met Phe Arg Glu Leu Val Gly Leu Pro Ala Gly
                20                  25                  30

Ser Pro Glu Phe Gln Arg His Arg Asp Lys Ile Val Gln Arg Cys Leu
            35                  40                  45

Pro Leu Ala Asp His Ile Ala Arg Arg Phe Glu Gly Arg Gly Glu Pro
        50                  55                  60

Arg Asp Asp Leu Ile Gln Val Ala Arg Val Gly Leu Val Asn Ala Ala
65                  70                  75                  80

Val Arg Phe Asp Val Lys Thr Gly Ser Asp Phe Val Ser Phe Ala Val
                85                  90                  95
```

-continued

```
Pro Thr Ile Met Gly Glu Val Arg Arg His Phe Arg Asp Asn Ser Trp
            100                 105                 110

Ser Val Lys Val Pro Arg Arg Leu Lys Glu Leu His Leu Arg Leu Gly
            115                 120                 125

Thr Ala Thr Ala Asp Leu Ser Gln Arg Leu Gly Arg Ala Pro Ser Ala
130                 135                 140

Ser Glu Leu Ala Ala Glu Leu Gly Met Asp Arg Ala Glu Val Ile Glu
145                 150                 155                 160

Gly Leu Leu Ala Gly Ser Ser Tyr His Thr Leu Ser Ile Asp Ser Gly
                165                 170                 175

Gly Gly Ser Asp Asp Asp Ala Arg Ala Ile Thr Asp Thr Leu Gly Asp
                180                 185                 190

Val Asp Ala Gly Leu Asp Gln Ile Glu Asn Arg Glu Val Leu Arg Pro
                195                 200                 205

Leu Leu Glu Ala Leu Pro Glu Arg Glu Arg Thr Val Leu Val Leu Arg
210                 215                 220

Phe Phe Asp Ser Met Thr Gln Thr Gln Ile Ala Glu Arg Val Gly Ile
225                 230                 235                 240

Ser Gln Met His Val Ser Arg Val Leu Ala Lys Ser Leu Ala Arg Leu
                245                 250                 255

Arg Asp Gln Leu Glu
            260
```

(2) INFORMATION FOR SEQ ID NO:3:

(i) SEQUENCE CHARACTERISTICS:
        (A) LENGTH: 242 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Mycobacterium tuberculosis (xi) SEQUENCE DESCRIPTION: SEQ ID NO:3:

```
Met Ala Ser Val Arg Ala Ser Ala Asp Thr Gln Asp Cys Arg Ser Leu
1               5                   10                  15

Val Tyr Arg Thr Ser Arg Ser Pro Ala Ala Ala Gly Arg Leu Asp
            20                  25                  30

Ile Leu Val Arg Leu Glu Ile Pro Ala Ser Arg Gly Phe Thr Gly Ser
            35                  40                  45

Cys Glu Trp Val Ser Arg Val His His Asp Glu Ser Arg Pro Cys Cys
    50                  55                  60

Val Arg Ser Pro Leu Pro Ala Gly Pro Thr Met Thr Asp Gln Leu Glu
65                  70                  75                  80

Asp Gln Thr Gln Gly Gly Ser Thr Val Asp Arg Ser Leu Pro Gly Gly
                85                  90                  95

Cys Met Ala Asp Ser Asp Leu Pro Thr Lys Gly Arg Gln Arg Gly Val
            100                 105                 110

Arg Ala Val Glu Leu Asn Val Ala Arg Leu Glu Asn Leu Ala Leu
            115                 120                 125

Leu Arg Thr Leu Val Gly Ala Ile Gly Thr Phe Glu Asp Leu Asp Phe
130                 135                 140

Asp Ala Val Ala Asp Leu Arg Leu Ala Val Asp Glu Val Cys Thr Arg
```

```
145                 150                 155                 160

Leu Ile Arg Ser Ala Leu Pro Asp Ala Thr Leu Arg Leu Val Val Asp
                165                 170                 175

Pro Arg Lys Asp Glu Val Val Glu Ala Ser Ala Ala Cys Asp Thr
            180                 185                 190

His Asp Val Val Ala Pro Gly Ser Phe Ser Trp His Val Leu Thr Ala
            195                 200                 205

Leu Ala Asp Asp Val Gln Thr Phe His Asp Gly Arg Gln Pro Asp Val
210                 215                 220

Ala Gly Ser Val Phe Gly Ile Thr Leu Thr Ala Arg Arg Ala Ala Ser
225                 230                 235                 240

Ser Arg (2) INFORMATION FOR SEQ ID NO:4:

(i) SEQUENCE CHARACTERISTICS:
        (A) LENGTH: 137 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Mycobacterium tuberculosis (xi) SEQUENCE DESCRIPTION: SEQ ID NO:4:

Met Gly Gln Ile Pro Pro Gln Pro Val Arg Arg Val Leu Pro Leu Met
1               5                   10                  15

Val Val Pro Gly Asn Gly Gln Lys Trp Arg Asn Arg Thr Glu Thr Glu
            20                  25                  30

Glu Ala Met Gly Asp Thr Tyr Arg Asp Pro Val Asp His Leu Arg Thr
        35                  40                  45

Thr Arg Pro Leu Ala Gly Glu Ser Leu Ile Asp Val Val His Trp Pro
    50                  55                  60

Gly Tyr Leu Leu Ile Val Ala Gly Val Val Gly Val Gly Ala Leu
65                  70                  75                  80

Ala Ala Phe Gly Thr Gly His His Ala Glu Gly Met Thr Phe Gly Val
                85                  90                  95

Val Ala Ile Val Val Thr Val Val Gly Leu Ala Trp Leu Ala Phe Glu
                100                 105                 110

His Arg Arg Ile Arg Lys Ile Ala Asp Arg Trp Tyr Thr Glu His Pro
            115                 120                 125

Glu Val Arg Arg Gln Arg Leu Ala Gly
        130                 135

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(vi) ORIGINAL SOURCE:
            (A) ORGANISM: Mycobacterium tuberculosis (xi) SEQUENCE DESCRIPTION: SEQ ID NO:5:

AACCTGCGHC TSGTSGTC                                                       18

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:6:

Asn Leu Arg Leu Val Val
1               5

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Mycobacterium tuberculosis (xi) SEQUENCE DESCRIPTION: SEQ ID NO:7:

CTGNCGKATC CACCASGTSG CRTA                                                24

(2) INFORMATION FOR SEQ ID NO:8:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:8:

Tyr Ala Thr Trp Trp Ile Arg Gln
1               5

(2) INFORMATION FOR SEQ ID NO:9:

(i) SEQUENCE CHARACTERISTICS:
        (A) LENGTH: 287 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Streptomyces coelicolor (xi) SEQUENCE DESCRIPTION: SEQ ID NO:9:

```
Met Pro Ala Ser Thr Ala Pro Gln Ala Pro Ala Pro Pro Ala Gln
1               5                  10                 15

Ala Gln Ala Gln Ala Pro Ala Gln Ala Gln Glu Ala Pro Ala Pro Gln
                20                  25                 30

Arg Ser Arg Gly Ala Asp Thr Arg Ala Leu Thr Gln Val Leu Phe Gly
            35                  40                  45

Glu Leu Lys Gly Leu Ala Pro Gly Thr Pro Glu His Asp Arg Val Arg
50                      55                  60

Ala Ala Leu Ile Glu Ala Asn Leu Pro Leu Val Arg Tyr Ala Ala Ala
65                      70                  75                  80

Arg Phe Arg Ser Arg Asn Glu Pro Met Glu Asp Val Val Gln Val Gly
                85                  90                  95

Thr Ile Gly Leu Ile Asn Ala Ile Asp Arg Phe Asp Pro Glu Arg Gly
                100                 105                 110

Val Gln Phe Pro Thr Phe Ala Met Pro Thr Val Gly Glu Ile Lys
                115                 120                 125

Arg Tyr Phe Arg Asp Asn Val Arg Thr Val His Val Pro Arg Arg Leu
130                 135                 140

His Glu Leu Trp Val Gln Val Asn Ser Ala Thr Glu Asp Leu Thr Thr
145                 150                 155                 160

Ala Phe Gly Arg Ser Pro Thr Thr Ala Glu Ile Ala Glu Arg Leu Arg
                165                 170                 175

Ile Thr Glu Glu Glu Val Leu Ser Cys Ile Glu Ala Gly Arg Ser Tyr
                180                 185                 190

His Ala Thr Ser Leu Glu Ala Ala Gln Glu Gly Asp Gly Leu Pro Gly
                195                 200                 205

Leu Leu Asp Arg Leu Gly Tyr Glu Asp Pro Ala Leu Asp Gly Val Glu
210                 215                 220

His Arg Asp Leu Val Arg His Leu Leu Val Gln Leu Pro Glu Arg Glu
225                 230                 235                 240

Gln Arg Ile Leu Leu Leu Arg Tyr Tyr Ser Asn Leu Thr Gln Ser Gln
                245                 250                 255

Ile Ser Ala Glu Leu Gly Val Ser Gln Met His Val Ser Arg Leu Leu
                260                 265                 270

Ala Arg Ser Phe Gln Arg Leu Arg Ser Ala Asn Arg Ile Asp Ala
                275                 280                 285

(2) INFORMATION FOR SEQ ID NO:10:

(i) SEQUENCE CHARACTERISTICS:
        (A) LENGTH: 255 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Bacillus subtilis (xi) SEQUENCE DESCRIPTION: SEQ ID NO:10:

Met Asp Val Glu Val Lys Lys Asn Gly Lys Asn Ala Gln Leu Lys Asp
1               5                   10                  15

His Glu Val Lys Glu Leu Ile Lys Gln Ser Gln Asn Gly Asp Gln Gln
                20                  25                  30

Ala Arg Asp Leu Leu Ile Glu Lys Asn Met Arg Leu Val Trp Ser Val
            35                  40                  45
```

-continued

```
Val Gln Arg Phe Leu Asn Arg Gly Tyr Glu Pro Asp Asp Leu Phe Gln
         50                  55                  60

Ile Gly Cys Ile Gly Leu Leu Lys Ser Val Asp Lys Phe Asp Leu Thr
 65                  70                  75                  80

Tyr Asp Val Arg Phe Ser Thr Tyr Ala Val Pro Met Ile Ile Gly Glu
                 85                  90                  95

Ile Gln Arg Phe Ile Arg Asp Asp Gly Thr Val Lys Val Ser Arg Ser
             100                 105                 110

Leu Lys Glu Leu Gly Asn Lys Ile Arg Arg Ala Lys Asp Glu Leu Ser
         115                 120                 125

Lys Thr Leu Gly Arg Val Pro Thr Val Gln Glu Ile Ala Asp His Leu
 130                 135                 140

Glu Ile Glu Ala Glu Asp Val Val Leu Ala Gln Glu Ala Val Arg Ala
145                 150                 155                 160

Pro Ser Ser Ile His Glu Thr Val Tyr Glu Asn Asp Gly Asp Pro Ile
                 165                 170                 175

Thr Leu Leu Asp Gln Ile Ala Asp Asn Ser Glu Glu Lys Trp Phe Asp
             180                 185                 190

Lys Ile Ala Leu Lys Glu Ala Ile Ser Asp Leu Glu Glu Arg Glu Lys
         195                 200                 205

Leu Ile Val Tyr Leu Arg Tyr Tyr Lys Asp Gln Thr Gln Ser Glu Val
 210                 215                 220

Ala Glu Arg Leu Gly Ile Ser Gln Val Gln Val Ser Arg Leu Glu Lys
225                 230                 235                 240

Lys Ile Leu Lys Gln Ile Lys Val Gln Met Asp His Thr Asp Gly
             245                 250                 255

(2) INFORMATION FOR SEQ ID NO:11:

(i) SEQUENCE CHARACTERISTICS:
        (A) LENGTH: 262 amino acids
        (B) TYPE: amino acid
        (D) TOPOLOGY: linear (ii) MOLECULE TYPE: protein (iii) HYPOTHETICAL: NO (vi) ORIGINAL SOURCE:
         (A) ORGANISM: Bacillus subtilis (xi) SEQUENCE DESCRIPTION: SEQ ID NO:11:

Met Thr Gln Pro Ser Lys Thr Thr Lys Leu Thr Lys Asp Glu Val Asp
 1               5                  10                  15

Arg Leu Ile Ser Asp Tyr Gln Thr Lys Gln Asp Glu Gln Ala Gln Glu
             20                  25                  30

Thr Leu Val Arg Val Tyr Thr Asn Leu Val Asp Met Leu Ala Lys Lys
         35                  40                  45

Tyr Ser Lys Gly Lys Ser Phe His Glu Asp Leu Arg Gln Val Gly Met
 50                  55                  60

Ile Gly Leu Leu Gly Ala Ile Lys Arg Tyr Asp Pro Val Val Gly Lys
 65                  70                  75                  80

Ser Phe Glu Ala Phe Ala Ile Pro Thr Ile Ile Gly Glu Ile Lys Arg
                 85                  90                  95

Phe Leu Arg Asp Lys Thr Trp Ser Val His Val Pro Arg Arg Ile Lys
             100                 105                 110

Glu Leu Gly Pro Arg Ile Lys Met Ala Val Asp Gln Leu Thr Thr Glu
         115                 120                 125
```

```
Thr Gln Arg Ser Pro Lys Val Glu Glu Ile Ala Glu Phe Leu Asp Val
    130                 135                 140
Ser Glu Glu Val Leu Glu Thr Met Glu Met Gly Lys Ser Tyr Gln
145                 150                 155                 160
Ala Leu Ser Val Asp His Ser Ile Glu Ala Asp Ser Asp Gly Ser Thr
                165                 170                 175
Val Thr Ile Leu Asp Ile Val Gly Ser Gln Glu Asp Gly Tyr Glu Arg
            180                 185                 190
Val Asn Gln Gln Leu Met Leu Gln Ser Val Leu His Val Leu Ser Asp
        195                 200                 205
Arg Glu Lys Gln Ile Ile Asp Leu Thr Tyr Ile Gln Asn Lys Ser Gln
    210                 215                 220
Lys Glu Thr Gly Asp Ile Leu Gly Ile Ser Gln Met His Val Ser Arg
225                 230                 235                 240
Leu Gln Arg Lys Ala Val Lys Lys Leu Arg Glu Ala Leu Ile Glu Asp
                245                 250                 255
Pro Ser Met Glu Leu Met
            260
```

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:12:

CATATGACGG CGCGCGCTGC CGGC                                            24

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:13:

ACTAGTTACT CCAACTGATC CCGTAG                                      26

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:14:

TCACCGGAAT TCGGATCCGT CGACCTG                                    27

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

AATTGTTTAA ACGCTTAATT                                                20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:16:

AATTAATTAA GCGTTTAAAC                                      20